(12) United States Patent
Zale et al.

(10) Patent No.: US 9,351,933 B2
(45) Date of Patent: *May 31, 2016

(54) THERAPEUTIC POLYMERIC NANOPARTICLES COMPRISING VINCA ALKALOIDS AND METHODS OF MAKING AND USING SAME

(71) Applicant: BIND Therapeutics, Inc., Cambridge, MA (US)

(72) Inventors: Stephen E. Zale, Hopkinton, MA (US); Greg Troiano, Pembroke, MA (US); Mir Mukkaram Ali, Woburn, MA (US); Jeff Hrkach, Lexington, MA (US); James Wright, Lexington, MA (US)

(73) Assignee: BIND Therapeutics, Inc., Cambridge, MA (US)

( * ) Notice: Subject to any disclaimer, the term of this patent is extended or adjusted under 35 U.S.C. 154(b) by 395 days.

This patent is subject to a terminal disclaimer.

(21) Appl. No.: 13/660,281

(22) Filed: Oct. 25, 2012

(65) Prior Publication Data

US 2013/0189315 A1    Jul. 25, 2013

Related U.S. Application Data

(63) Continuation of application No. 12/485,467, filed on Jun. 16, 2009, now Pat. No. 8,318,211.

(60) Provisional application No. 61/061,704, filed on Jun. 16, 2008, provisional application No. 61/061,697, filed on Jun. 16, 2008, provisional application No. 61/061,760, filed on Jun. 16, 2008, provisional application No. 61/088,159, filed on Aug. 12, 2008, provisional application No. 61/105,916, filed on Oct. 16, 2008, provisional application No. 61/106,777, filed on Oct. 20, 2008, provisional application No. 61/169,514, filed on Apr. 15, 2009, provisional application No. 61/169,519, filed on Apr. 15, 2009, provisional application No. 61/169,541, filed on Apr. 15, 2009, provisional application No. 61/173,784, filed on Apr. 29, 2009, provisional application No. 61/175,209, filed on May 4, 2009, provisional application No. 61/175,219, filed on May 4, 2009, provisional application No. 61/175,226, filed on May 4, 2009, provisional application No. 61/182,300, filed on May 29, 2009.

(51) Int. Cl.
| | |
|---|---|
| *A61K 9/14* | (2006.01) |
| *A61K 31/4745* | (2006.01) |
| *A61K 31/475* | (2006.01) |
| *A61K 9/19* | (2006.01) |
| *A61K 9/51* | (2006.01) |
| *A61K 31/55* | (2006.01) |

(52) U.S. Cl.
CPC ... *A61K 9/14* (2013.01); *A61K 9/19* (2013.01); *A61K 9/5153* (2013.01); *A61K 31/475* (2013.01); *A61K 31/4745* (2013.01); *A61K 31/55* (2013.01)

(58) Field of Classification Search
None
See application file for complete search history.

(56) References Cited

U.S. PATENT DOCUMENTS

| | | | |
|---|---|---|---|
| 5,302,401 | A | 4/1994 | Liversidge et al. |
| 5,543,158 | A | 8/1996 | Gref et al. |
| 5,563,122 | A | 10/1996 | Endo et al. |
| 5,578,325 | A | 11/1996 | Domb et al. |
| 5,766,635 | A | 6/1998 | Spenleuhauer et al. |
| 6,007,845 | A | 12/1999 | Domb et al. |
| 6,136,846 | A | 10/2000 | Rubinfeld et al. |
| 6,139,870 | A | 10/2000 | Verrecchia |
| 6,194,006 | B1 | 2/2001 | Lyons et al. |
| 6,201,072 | B1 | 3/2001 | Rathi et al. |
| 6,254,890 | B1 | 7/2001 | Hirosue et al. |
| 6,265,609 | B1 | 7/2001 | Jackson et al. |
| 6,346,274 | B1 | 2/2002 | Koll et al. |
| 6,395,718 | B1 | 5/2002 | Slusher et al. |
| 6,528,499 | B1 | 3/2003 | Kozikowski et al. |
| 6,841,547 | B2 | 1/2005 | Brown et al. |
| 6,875,886 | B2 | 4/2005 | Frangioni |
| 6,890,946 | B2 | 5/2005 | Nakshatri et al. |
| 6,890,950 | B2 | 5/2005 | Boothman et al. |
| 6,899,898 | B2 | 5/2005 | Albayrak |
| 6,902,743 | B1 | 6/2005 | Setterstrom et al. |
| 6,916,788 | B2 | 7/2005 | Seo et al. |
| 7,422,902 | B1 | 9/2008 | Wheeler et al. |
| 7,687,071 | B1 | 3/2010 | Heger et al. |
| 8,003,128 | B2 | 8/2011 | Kreuter et al. |

(Continued)

FOREIGN PATENT DOCUMENTS

| | | |
|---|---|---|
| CN | 1957911 A | 5/2007 |
| CN | 1961864 A | 5/2007 |

(Continued)

OTHER PUBLICATIONS

Govender et al., "Defining the drug incorporation properties of PLA-PEG nanoparticles", 2000, International Journal of Pharmaceutics, vol. 199, pp. 95-110.*

(Continued)

*Primary Examiner* — Michael B Pallay

(74) *Attorney, Agent, or Firm* — Goodwin Procter LLP

(57) ABSTRACT

The present disclosure generally relates to therapeutic nanoparticles. Exemplary nanoparticles disclosed herein may include about 1 to about 20 weight percent of a vinca alkaloid; and about 50 to about 99 weight percent biocompatible polymer.

23 Claims, 10 Drawing Sheets

(56) References Cited

U.S. PATENT DOCUMENTS

| | | | |
|---|---|---|---|
| 8,034,765 B2 | 10/2011 | De et al. | |
| 8,206,747 B2 | 6/2012 | Zale et al. | |
| 8,211,473 B2 | 7/2012 | Troiano et al. | |
| 8,236,330 B2 | 8/2012 | Zale et al. | |
| 8,246,968 B2 | 8/2012 | Zale et al. | |
| 8,273,363 B2 | 9/2012 | Zale et al. | |
| 8,293,276 B2 | 10/2012 | Troiano et al. | |
| 8,318,208 B1* | 11/2012 | Zale et al. | 424/489 |
| 8,318,211 B2* | 11/2012 | Zale et al. | 424/501 |
| 8,357,401 B2 | 1/2013 | Troiano et al. | |
| 8,420,123 B2 | 4/2013 | Troiano et al. | |
| 8,518,963 B2* | 8/2013 | Ali et al. | 514/283 |
| 8,603,534 B2* | 12/2013 | Zale et al. | 424/489 |
| 8,613,951 B2 | 12/2013 | Zale et al. | |
| 8,617,608 B2* | 12/2013 | Zale et al. | 424/489 |
| 8,623,417 B1 | 1/2014 | Zale et al. | |
| 8,912,212 B2* | 12/2014 | Zale et al. | 514/283 |
| 8,956,657 B2* | 2/2015 | Troiano et al. | 424/489 |
| 2002/0045582 A1 | 4/2002 | Margolin et al. | |
| 2002/0119916 A1 | 8/2002 | Hassan | |
| 2003/0068377 A1 | 4/2003 | Fowers et al. | |
| 2003/0143184 A1 | 7/2003 | Seo et al. | |
| 2003/0232887 A1 | 12/2003 | Johnson et al. | |
| 2003/0235619 A1 | 12/2003 | Allen et al. | |
| 2004/0054190 A1 | 3/2004 | Pomper et al. | |
| 2004/0071768 A1 | 4/2004 | Sarris et al. | |
| 2004/0081688 A1 | 4/2004 | Del Curto et al. | |
| 2004/0086544 A1 | 5/2004 | Bezemer et al. | |
| 2004/0185170 A1 | 9/2004 | Chungi et al. | |
| 2004/0219224 A1 | 11/2004 | Yakovlevsky et al. | |
| 2004/0220081 A1 | 11/2004 | Kreitz et al. | |
| 2004/0247624 A1 | 12/2004 | Unger et al. | |
| 2004/0247680 A1 | 12/2004 | Farokhzad et al. | |
| 2005/0037075 A1 | 2/2005 | Farokhzad et al. | |
| 2005/0037086 A1 | 2/2005 | Tyo et al. | |
| 2005/0063976 A1 | 3/2005 | Schultes et al. | |
| 2005/0123617 A1 | 6/2005 | Chang et al. | |
| 2005/0136258 A1 | 6/2005 | Nie et al. | |
| 2005/0142205 A1 | 6/2005 | Rashba-Step et al. | |
| 2005/0201972 A1 | 9/2005 | Seo et al. | |
| 2005/0256071 A1 | 11/2005 | Davis | |
| 2005/0266067 A1 | 12/2005 | Sengupta et al. | |
| 2006/0002852 A1 | 1/2006 | Saltzman et al. | |
| 2006/0002971 A1 | 1/2006 | Saltzman et al. | |
| 2006/0034925 A1 | 2/2006 | Au et al. | |
| 2006/0057219 A1 | 3/2006 | Nagasaki et al. | |
| 2006/0110460 A1 | 5/2006 | Ferret et al. | |
| 2006/0165987 A1 | 7/2006 | Hildgen et al. | |
| 2007/0031402 A1 | 2/2007 | Zhang et al. | |
| 2007/0041901 A1 | 2/2007 | Diener et al. | |
| 2007/0043066 A1 | 2/2007 | Sum et al. | |
| 2007/0053845 A1 | 3/2007 | Sengupta et al. | |
| 2007/0154554 A1 | 7/2007 | Burgermeister et al. | |
| 2008/0057102 A1 | 3/2008 | Roorda | |
| 2008/0081074 A1 | 4/2008 | Gu et al. | |
| 2008/0124400 A1 | 5/2008 | Liggins et al. | |
| 2008/0193381 A1 | 8/2008 | Babich et al. | |
| 2008/0267876 A1 | 10/2008 | Benita et al. | |
| 2009/0022806 A1 | 1/2009 | Mousa et al. | |
| 2009/0053293 A1* | 2/2009 | Liang et al. | 424/450 |
| 2009/0053315 A1 | 2/2009 | Brough et al. | |
| 2009/0061009 A1 | 3/2009 | Schwarz et al. | |
| 2009/0061010 A1 | 3/2009 | Zale et al. | |
| 2009/0074753 A1 | 3/2009 | Lynch | |
| 2009/0074828 A1 | 3/2009 | Alexis et al. | |
| 2009/0155349 A1 | 6/2009 | Heller et al. | |
| 2009/0170753 A1 | 7/2009 | Welz et al. | |
| 2009/0196933 A1 | 8/2009 | De et al. | |
| 2009/0306120 A1 | 12/2009 | Lim et al. | |
| 2009/0317479 A1 | 12/2009 | Ishihara et al. | |
| 2010/0008998 A1 | 1/2010 | Kang et al. | |
| 2010/0015050 A1 | 1/2010 | Panyam et al. | |
| 2010/0040537 A1 | 2/2010 | Gu et al. | |
| 2010/0068285 A1 | 3/2010 | Zale et al. | |
| 2010/0068286 A1 | 3/2010 | Troiano et al. | |
| 2010/0069426 A1 | 3/2010 | Zale et al. | |
| 2010/0087337 A1 | 4/2010 | Dewitt | |
| 2010/0104645 A1 | 4/2010 | Ali et al. | |
| 2010/0104655 A1 | 4/2010 | Zale et al. | |
| 2010/0166866 A1 | 7/2010 | Fischer et al. | |
| 2010/0216804 A1 | 8/2010 | Zale et al. | |
| 2010/0226986 A1 | 9/2010 | Grayson et al. | |
| 2010/0266491 A1 | 10/2010 | Farokhzad et al. | |
| 2010/0303723 A1 | 12/2010 | Farokhzad et al. | |
| 2010/0303900 A1 | 12/2010 | Ramstack et al. | |
| 2010/0316725 A1 | 12/2010 | Ryde et al. | |
| 2011/0159079 A1 | 6/2011 | Li et al. | |
| 2011/0217377 A1 | 9/2011 | Zale et al. | |
| 2011/0224288 A1 | 9/2011 | Zale et al. | |
| 2011/0274759 A1 | 11/2011 | Troiano et al. | |
| 2011/0275704 A1 | 11/2011 | Troiano et al. | |
| 2011/0294717 A1 | 12/2011 | Ali et al. | |
| 2012/0004293 A1 | 1/2012 | Zale et al. | |
| 2012/0027820 A1 | 2/2012 | Troiano et al. | |
| 2012/0140790 A1 | 6/2012 | Ali et al. | |
| 2012/0276162 A1 | 11/2012 | Zale et al. | |
| 2013/0034608 A1 | 2/2013 | Zale et al. | |
| 2013/0101672 A1 | 4/2013 | Cheng et al. | |
| 2013/0108668 A1 | 5/2013 | Figueiredo et al. | |
| 2013/0115293 A1 | 5/2013 | Sabnis et al. | |
| 2013/0172406 A1 | 7/2013 | Zale et al. | |
| 2013/0189315 A1 | 7/2013 | Zale et al. | |
| 2013/0230567 A1 | 9/2013 | Zale et al. | |
| 2013/0230568 A1 | 9/2013 | Troiano et al. | |
| 2013/0236500 A1 | 9/2013 | Zale et al. | |
| 2013/0243827 A1 | 9/2013 | Troiano et al. | |
| 2013/0243863 A1 | 9/2013 | Troiano et al. | |
| 2013/0251757 A1 | 9/2013 | Troiano et al. | |
| 2013/0280339 A1 | 10/2013 | Zale et al. | |
| 2013/0295183 A1 | 11/2013 | Troiano et al. | |
| 2013/0295191 A1 | 11/2013 | Troiano et al. | |
| 2013/0302432 A1 | 11/2013 | Zale et al. | |
| 2013/0302433 A1 | 11/2013 | Troiano et al. | |
| 2014/0030351 A1 | 1/2014 | Zale et al. | |
| 2014/0093579 A1 | 4/2014 | Zale et al. | |
| 2014/0142165 A1 | 5/2014 | Grayson et al. | |
| 2014/0178475 A1 | 6/2014 | Figueiredo et al. | |
| 2014/0186452 A1 | 7/2014 | Figueiredo et al. | |
| 2014/0186453 A1 | 7/2014 | Zale et al. | |
| 2014/0248358 A1 | 9/2014 | Figueiredo et al. | |
| 2014/0249158 A1 | 9/2014 | Figueiredo et al. | |
| 2014/0308363 A1 | 10/2014 | Zale | |
| 2014/0356444 A1 | 12/2014 | Troiano et al. | |

FOREIGN PATENT DOCUMENTS

| | | |
|---|---|---|
| CN | 1969816 A | 5/2007 |
| CN | 1969818 A | 5/2007 |
| CN | 101053553 A | 10/2007 |
| CN | 101396340 A | 4/2009 |
| CN | 101396342 A | 4/2009 |
| CN | 101433520 A | 5/2009 |
| EA | 011594 | 12/2007 |
| EP | 0805678 A1 | 11/1997 |
| EP | 1985309 A1 | 10/2008 |
| EP | 2106806 A1 | 10/2009 |
| JP | H10-194995 A | 7/1998 |
| JP | 2006131577 A | 5/2006 |
| JP | 2006321763 A | 11/2006 |
| KR | 10-0418916 | 3/2002 |
| KR | 20020041712 A | 6/2002 |
| RU | 2007/140909 A | 5/2009 |
| WO | WO-8900846 A1 | 2/1989 |
| WO | WO-9428874 A1 | 12/1994 |
| WO | WO-9503357 A1 | 2/1995 |
| WO | WO-9535097 A1 | 12/1995 |
| WO | WO-9741837 A2 | 11/1997 |
| WO | WO-00/00222 A1 | 1/2000 |
| WO | WO-0019996 A1 | 4/2000 |
| WO | WO-0187345 A1 | 11/2001 |
| WO | WO-0245689 A1 | 6/2002 |
| WO | WO-02080846 A2 | 10/2002 |
| WO | WO-02/098885 A1 | 12/2002 |
| WO | WO-03017987 A1 | 3/2003 |

(56) References Cited

FOREIGN PATENT DOCUMENTS

| | | |
|---|---|---|
| WO | WO-03032906 A2 | 4/2003 |
| WO | WO-03/055469 A1 | 7/2003 |
| WO | WO-03/086369 A2 | 10/2003 |
| WO | WO-2004060059 A2 | 7/2004 |
| WO | WO-2004/084871 A1 | 10/2004 |
| WO | WO-2004089291 A2 | 10/2004 |
| WO | WO-2005009357 A2 | 2/2005 |
| WO | WO-2005020989 A1 | 3/2005 |
| WO | WO-2005/046572 A2 | 5/2005 |
| WO | WO-2006/093991 A1 | 9/2006 |
| WO | WO-2007/024323 A2 | 3/2007 |
| WO | WO-2007/028341 A1 | 3/2007 |
| WO | WO-2007/034479 A2 | 3/2007 |
| WO | WO 2007028341 A1 * | 3/2007 ........... A61K 31/475 |
| WO | WO-2007/074604 A1 | 7/2007 |
| WO | WO-2007/110152 A2 | 10/2007 |
| WO | WO-2007/133807 A2 | 11/2007 |
| WO | WO-2008/019142 A2 | 2/2008 |
| WO | WO-2008016602 A2 | 2/2008 |
| WO | WO-2008/058192 A2 | 5/2008 |
| WO | WO-2008051245 A2 | 5/2008 |
| WO | WO-2008/105773 A2 | 9/2008 |
| WO | WO-2008109163 A1 | 9/2008 |
| WO | WO-2008/121949 A1 | 10/2008 |
| WO | WO-2008/124632 A1 | 10/2008 |
| WO | WO-2008/124634 A1 | 10/2008 |
| WO | WO-2008/124639 A2 | 10/2008 |
| WO | WO-2008/139804 A1 | 11/2008 |
| WO | WO-2009/070302 A1 | 6/2009 |
| WO | WO-2009074274 A1 | 6/2009 |
| WO | WO-2009/084801 A1 | 7/2009 |
| WO | WO-2009121631 A2 | 10/2009 |
| WO | WO-2010/005721 A2 | 1/2010 |
| WO | WO-2010/005723 A2 | 1/2010 |
| WO | WO-2010/005725 A2 | 1/2010 |
| WO | WO-2010/005726 A2 | 1/2010 |
| WO | WO-2010/068866 A2 | 6/2010 |
| WO | WO-2010/075072 A2 | 7/2010 |
| WO | WO-2010/114768 A1 | 10/2010 |
| WO | WO-2010/114770 A1 | 10/2010 |
| WO | WO-2010117668 A1 | 10/2010 |
| WO | WO-2011/072218 A2 | 6/2011 |
| WO | WO-2011/079279 A2 | 6/2011 |
| WO | WO-2011/084513 A2 | 7/2011 |
| WO | WO-2011/084518 A2 | 7/2011 |
| WO | WO-2011/084521 A2 | 7/2011 |
| WO | WO-2011/119995 A2 | 9/2011 |
| WO | WO-2012040513 A1 | 3/2012 |
| WO | WO-2012/054923 A2 | 4/2012 |
| WO | WO-2012/166923 A2 | 12/2012 |
| WO | WO-2013/044219 A1 | 3/2013 |
| WO | WO-2013127490 A1 | 9/2013 |
| WO | WO-2014043618 A1 | 3/2014 |
| WO | WO-2014043625 A1 | 3/2014 |
| WO | WO-2014210485 A1 | 12/2014 |

OTHER PUBLICATIONS

Extended European Search Report for EP 11835279.8 mailed Feb. 28, 2014, 8 pages.
International Search Report for Application No. PCT/US2013/059936, dated Feb. 4, 2014 and mailed Feb. 4, 2014, 8 pages.
International Search Report for Application No. PCT/US2013/059949, dated Jan. 2, 2014 and mailed Jan. 2, 2014, 5 pages.
Kimura et al., "Local Delivery of Imatinib Mesylate (STI571)-Incorporated Nanoparticle Ex Vivo Suppresses Vein Graft Neointima Formation," *Cancer Res.* (2008) 118:S65-S70.
Li et al. "Post-Operative Imatinib in Patients with Intermediate or High Risk Gastrointestinal Stromal Tumor," *EJSO.* (2011) 37:319-324.
Abdelwahed et al., "Freeze-Drying of Nanoparticles: Formulation, Process and Storage Considerations," *Adv. Drug Deliv. Rev.* (2006) 58:1688-1713.
Abizaid et al., "Sirolimus-Eluting Stents Inhibits Neointimal Hyperplasia in Diabetic Patients," *Eur. Heart J.* (2006) 25:104-112.
Adams et al., "Amphiphilic Block Copolymers for Drug Delivery", *J. Pharm. Sci.* (2003) 92, 1343-1355.
Barinka et al., "Interactions Between Human Glutamate Carboxypeptidase II and Urea-Based Inhibitors: Structural Characterization," *J. Med. Chem.* (2008) 51:7737-7743.
Barinka et al., "Structural Insight into the Pharmacophore Pocket of Human Glutamate Carboxypeptidase II," *J. Med. Chem.* (2007) 50:3267-3273.
Bilati et al., "Nanoprecipitation Versus Emulsion-based Techniques for the Encapsulation of Proteins into Biodegradable Nanoparticles and Process-related Stability Issues," AAPS *PharmSciTech.* (2005) 6(4):E594-E604.
Blindt et al., "A Novel Drug-Eluting Stent Coated with an Integrin-Binding Cyclic Arg-Gly-Asp Peptide Inhibits Neointimal Hyperplasia by Recruiting Endothelial Progenitor Cells," *J. Amer. Coll. Cardiol.* (2006) 47(9):1786-1795.
Caliceti et al., "Effective Protein Release from PEG/PLA Nanoparticles Produced by Compressed Gas Anti-Solvent Precipitation Techniques," *Journal of Controlled Release.* (2004) 94:195-205.
Chandran, et al., "Characterization of a Targeted Nanoparticle Functionalized with a Urea-Based Inhibitor of Prostate-Specific Membrane Antigen (PSMA)," *Cancer Biol. Ther.* (2008) 7:4:1-9.
Chen et al., "Radiohalogenated Prostate-Specific Membrane Antigen (PSMA)-Based Ureas as Imaging Agents for Prostate Cancer," *J. Med. Chem.* (2008) 51(24):7933-7943.
Cheng et al., "Formulation of Functionalized PLGA-PEG Nanoparticles for in Vivo Targeted Drug Delivery," *Biomaterials.* (2007) 28:869-879.
Dancey et al., "Therapeutic Targets" mTOR and Related Pathways, *Cancer Biol. Ther.* (2006) 5:9: 1065-1073.
Davaran, "Preparation and in Vitro Evaluation of Linear and Star-Branched PLGA Nanoparticles for Insulin Delivery," *J. Bioact. Compat. Polym.* (2008) 23:115-131.
De Jaeghere et al., "Formulation and Lyoprotection of Poly(lactic acid-co-ethylene oxide) Nanoparticles: Influence on Physical Stability and in Vitro Cell Uptake," *Pharm. Res.* (1999) 16(6):859-866.
De Jaeghere et al., "Freeze-Drying and Lyopreservation of Diblock and Triblock Poly(Lactic Acid)-Poly(Ethylene Oxide) (PLA-PEO) Copolymer Nanoparticles," *Pharmaceutical Development and Technology.* (2000) 5(4):473-483.
"Docetaxel Dosage," [retrieved on Mar. 28, 2013] http://www.drugs.com/dosage/docetaxel.html.
Eurasian Search Report for Application No. EA 201170038, dated Jul. 8, 2011.
Eurasian Search Report for Application No. EA 201170039, dated Nov. 21, 2011.
Ewesuedo et al., "Chapter 1: Systemically Administrated Drugs." *Drug Delivery Systems in Cancer Therapy.* Ed. D.M. Brown. Totowa:Humana, 2003, pp. 3-14.
Extended European Search Report for Application No. EP 09794913.5 mailed Jul. 8, 2011.
Extended European Search Report for Application No. EP 09794915.0, mailed Jan. 25, 2012.
Extended European Search Report for Application No. EP 09835578.7, mailed May 18, 2012.
Extended European Search Report for Application No. EP 11186037.5, mailed Mar. 2, 2012.
Extended European Search Report for Application No. EP 10836748.3, mailed Mar. 21, 2013.
Farokhzad et al., "Nanoparticle-Aptamer Bioconjugates: A New Approach for Targeting Prostate Cancer Cells," *Cancer Res.* (Nov. 1, 2004) 64:7668-7672.
Farokhzad et al., "Targeted Nanoparticle-Aptamer Bioconjugates for Cancer Chemotherapy In Vivo," *Proc. Natl. Acad. Sci. USA.* (2006) 103(16):6315-6320.
Feng et al., "Nanoparticles of Biodegradable Polymers for Clinical Administration of Paclitaxel," *Current Medicinal Chemistry.* (2004) 11:413-424.
Foss et al., "Radiolabeled Small-Molecule Ligands for Prostate-Specific Membrane Antigen: In Vivo Imaging in Experimental Models of Prostate Cancer," *Clin. Cancer Res.* (2005) 11(11):4022-4028.

(56) References Cited

OTHER PUBLICATIONS

Foss, Poster Session: Novel Probes and Activation Strategies, Part 3, "Synthesis and Validation of a Novel Small-Molecule Fluorescent Probe for PSMA Expression in Human Tumor Neovasculature," 4th Annual Meeting for the Society for Molecular Imaging, (Sep. 7-10, 2005.).
Fournier et al., "Experimental Studies and Preliminary Clinical Trial of Vinorelbine-loaded Polymeric Bioresorbable Implants for the Local Treatment of Solid Tumors," *Cancer Research*. (1991) 51:5384-5391.
Galsky et al., "Cabazitaxel," *Nature Reviews*. (2010) 9:677-678.
Gao et al., "In Vivo Cancer Targeting and Imaging with Semiconductor Quantum Dots," *Nat. Biotechnol*. (2004) 22, 8: 969-976.
Zhou et al., "NAAG Peptidase Inhibitors and Their Potential for Diagnosis and Therapy," *Nature Rev. Drug Discov*. (2005) 4:1015-1026.
Govender et al., "Defining the Drug Incorporation Properties of PLA-PEG Nanoparticles," *Int. J. Pharm*. (2000) 199:95-110.
Gref et al., "Biodegradable Long-Circulating Polymeric Nanospheres," *Science*. (1994) 263:1600-1603.
Gref et al., "Development and Characterization of CyA-loaded Poly(lactic acid)-poly(ethylene glycol)PEG Micro- and Nanoparticles. Comparison with Conventional PLA Particulate Carriers." *Eur. J. Pharm. Biopharm*. (2001) 51:111-118.
Gu et al., "Precise Engineering of Targeted Nanoparticles by Using Self-Assembled Biointegrated Block Copolymers", *Proc. Natl. Acad. Sci. USA*. (2008) 105:2586-2591.
Heald et al., "Poly(lactic acid)-Poly(ethylene oxide) (PLA-PEG) Nanoparticles: NMR Studies of the Central Solidlike PLA Core and the Liquid PEG Corona," *Langmuir*. (2002) 18:3669-3675.
Hederstrom et al., "Purification and Surface Modification of Polymeric Nanoparticles for Medical Applications" Master's Thesis. SINTEF Materials and Chemistry, Trondheim, Norway, Mar. 3, 2008.
Heldman et al., "Paclitaxel stent coating inhibits neointimal hyperplasia at 4 weeks in a porcine model of coronary restenosis," *Circulation*. (2001) 103:2289-2295.
Hrkach et al., "Preclinical Development and Clinical Translation of a PSMA-Targeted Docetaxel Nanoparticle with a Differentiated Pharmacological Profile," *Sci. Trans. Med*. (2012) 4:1-11.
Humblet et al., "An HPLC/Mass Spectrometry Platform for the Development of Multimodality Contrast Agents and Targeted Therapeutics: Prostate-Specific Membrane Antigen Small Molecule Derivatives," *Contrast Med. Mol. Imaging*. (2006) 1:196-211.
Humblet et al., "High-Affinity Near-Infrared Fluorescent Small-Molecule Contrast Agents for In Vivo Imaging of Prostate-Specific Membrane Antigen," *Mol. Imaging*. ( 2005) 4:448-462.
International Search Report for Application No. PCT/US08/13158 dated Jan. 20, 2009 and mailed Feb. 17, 2009.
International Search Report for Application No. PCT/US08/58873 dated Aug. 15, 2008 and mailed Aug. 28, 2008.
International Search Report for Application No. PCT/US09/47513 dated Jan. 18, 2010 and mailed Jan. 18, 2010.
International Search Report for Application No. PCT/US09/67672 dated Aug. 20, 2010 and mailed Aug. 23, 2010.
International Search Report for Application No. PCT/US09/68028 dated Aug. 9, 2010 and mailed Aug. 23, 2010.
International Search Report for Application No. PCT/US10/59879 dated Aug. 30, 2011 and mailed Aug. 30, 2011.
International Search Report for Application No. PCT/US10/60564 dated Sep. 29, 2011 and mailed Sep. 29, 2011.
International Search Report for Application No. PCT/US10/60570 dated Aug. 25, 2011 and mailed Aug. 25, 2011.
International Search Report for Application No. PCT/US10/60575 dated Aug. 25, 2011 and mailed Aug. 25, 2011.
International Search Report for Application No. PCT/US11/057498 dated May 9, 2012 and mailed May 10, 2012.
International Search Report for Application No. PCT/US2012/040215 dated Nov. 16, 2012 and mailed Nov. 16, 2012.
International Search Report for Application No. PCT/US2012/056891 dated Jan. 4, 2013 and mailed Jan. 4, 2013.
International Search Report for PCT/US09/47515 dated Jan. 18, 2010 and mailed Jan. 19, 2010.
International Search Report for PCT/US09/47517 dated Feb. 23, 2010 and mailed Mar. 2, 2010.
International Search Report for PCT/US09/47518 dated Mar. 5, 2010 and mailed Mar. 5, 2010.
Jayaprakash et al., "Design and Synthesis of a PSMA Inhibitor-Doxorubicin Conjugate for Targeted Prostrate Cancer Therapy," ChemMedChem 2006, 1, pp. 299-302.
Jeong et al., "Effect of cryoprotectants on the reconstitution of surfactant-free nanoparticles of poly(DL-lactide-co-glycolide)," *J. of Microencapsulation*. (2005) 22(6):593-601.
Jiang et al., "Preparation of PLA and PLGA Nanoparticles by Binary Organic Solvent Diffusion Method," *J. Cent. South Univ. Technol*. (2003) 10(3):202-206.
Konstantinos Avgoustakis, "Pegylated poly(lactide) and poly(lactide-co-glycolide) nanoparticles: Preparation, properties and possible applications in drug delivery," *Current Drug Delivery*. (2004) 1(4):321-333.
Koziara et al., "Blood Compatibility of Cetyl Alcohol/Polysorbate-Based Nanoparticles," *Pharma. Res*. (2005) 22(11):1821-1828.
Kozikowski et al., Design of Remarkably Simple, Yet Potent Urea-Based Inhibitors of Glutamate Carboxypeptidase II (NAALADase), *J. Med. Chem*. (2001) 44:298-301.
Kozikowski et al., "Synthesis of Urea-Based Inhibitors as Active Site Probes of Glutamate Carboxypeptidase II: Efficacy as Analgesic Agents," *J. Med. Chem*. (2004) 47:1729-1738.
Kwon, "Long Acting Porous Microparticle for Pulmonary Protein Delivery," *Int. J. Pharm*. (2007) 333:5-9.
Lyseng-Williamson et al., "Docetaxel a Review of its Use in Metastatic Breast Cancer," *Drugs*. (2005) 65(17):2513-16.
Maresca et al., "A Series of Halogenated Heterodimeric Inhibitors of Prostate Specific Membrane Antigen (PSMA) as Radiolabeled Probes for Targeting Prostate Cancer," *J. Med. Chem*. (2009) 52(2):347-57.
Majer et al., "Synthesis and Biological Evaluation of Thiol-Based Inhibitors of Glutamate Carboxypeptidase II: Discovery of an Orally Active GCP II Inhibitor," *J. Med. Chem*. (2003) 46:1989-1996.
Mease et al., "N-[N-[(S)-1,3-Dicarboxypropyl] Carbamoyl]-4-[18F] Fluorobenzyl-L-Cysteine, [18F] DCFBC: A New Imaging Probe for Prostate Cancer," *Clin. Cancer Res*. (2008) 14(10):3036-3043.
Misra et al., "Production of Multimeric Prostate-Specific Membrane Antigen Small-Molecule Radiotracers Using a Solid-Phase 99m Tc Preloading Strategy," *J. Nuclear Med*. (2007) 48(8):379-1389.
Murugesan et al., Pegylated Poly(lactide-co-glycolidel (PLGA) Nanoparticulate Delivery of Docetaxel: Synthesis of Diblock Copolymers, Optimization of Preparation Variables on Formulation Characteristics and in Vitro Release Studies. *J. Biomed. Nanotechnol*. (2007) 3:52-60.
Musumeci et al., "Lyoprotected Nanosphere Formulations for Paclitaxel Controlled Delivery." *J. Nanosci. Nanotech*. (2006) 6:3118-3125.
Musumeci et al., "PLA/PLGA Nanoparticles for Sustained Release of Docetaxel," *Int. J. Pharm*. (2006) 325:172-179.
Ojer, "Spray-Drying of Poly(anhydride) Nanoparticles for Drug/Antigen Delivery," *J. Drug Del. Sci. Tech*. (2010) 20(5):353-359.
Oliver et al., "Conformational and SAR Analysis of NAALADase and PSMA Inhibitors," *Biorg. Med. Chem*. (2003) 11:4455-4461.
Olivier, "Drug Transport to Brain with Targeted Nanoparticles," *The Journal of the American Society for Experimental NeuroTherapeutics*. (2005) 2:108-119.
Omelczuk et al., "The Influence of Polymer Glass Transition Temperature and Molecular Weight on Drug Release from Tablets Containing Poly(DL-lactic acid)." *Pharm. Res*. (1992) 9(1):26-32.
Peracchia et al., "PEG-coated nanospheres from amphiphilic diblock and multiblock copolymers: Investigation of their drug encapsulation and release characteristics," *Journal of Controlled Release*. (1996) 46:223-231.
Pomper, Martin G., Russell H. Morgan Department of Radiology and Radiological Science, Johns Hopkins University, "New Develop-

(56) References Cited

OTHER PUBLICATIONS ments in Molecular Imaging of Prostate Cancer," Topical Symposium on: Advanced Molecular Imaging Techniques in the Detection, Diagnosis, Therapy, and Follow-up of Prostate Cancer, Palazzo Barberini, Rome, Dec. 6, 2005.

Pourcelle, "PCL-PEG-based Nanoparticles Grafted with GRGDS Peptide: Preparation and Surface Analysis by XPS," *Biomacromolecules*. (2007) 8:3977-3983.

Pulkkinen et al., "Three-Step Tumor Targeting of Paclitaxel Using Biotinylated PLA-PEG Nanoparticles and Avidin-Biotin Technology: Formulation Development and In Vitro Anticancer Activity", *Eur. J. Pharm. Biopharm*. (2008) 70:66-74.

Riley et al., "Colloidal Stability and Drug Incorporation Aspects of Micellar-like PLA-PEG Nanoparticles," *Colloids Surf. B: Biointer*. (1999) 16:147-59.

Sapra et al., "Ligand-Targeted Liposomal Anticancer Drugs," *Prog. Lipid Res*. (2003) 42:439-462.

Senthilkumar et al., "Long Circulating PEGylated Poly(D,L-lactide-co-glycolide) Nanoparticulate Delivery of Docetaxel to Solid Tumors," *J. Drug Target*. (2008) 424-435.

Sweetman, "Martindale: The Complete Drug Reference," 33rd ed., 2002, Pharmaceutical Press, entry for Docetaxel, p. 534.

Tamilvanan et al., "Manufacturing Techniques and Excipients Used During the Design of Biodegradable Polymer-Based Microspheres Containing Therapeutic Peptide/Protein for Parenteral Controlled Drug Delivery," *J. Pharm. Sci. Tech*. (2008) 62(2):125-154.

Tang, Hailun, et al., "Prostate Targeting Ligands Based on N-Acetylated α-Linked Acidic Dipeptidase," *Biochem. Biophys. Res. Comm*. 307 (2003), pp. 8-14.

"Taxotere Dosage," [retrieved on Mar. 28, 2013]. http://www.drugs.com/dosage/taxotere.html.

Tobio et al., "Stealth PLA-PEG Nanoparticles as Protein Carriers for Nasal Administration," *Pharm. Res*. (1998) 15(2):270-275.

Vicari et al., "Paclitaxel Loading in PLGA Nanospheres Affected the in Vitro Drug Cell Accumulation and Antiproliferative Activity," *BMC Cancer*. (2008) 8:212.

Yamamoto et al., "Long-Circulating Poly(ethylene glycol)-poly(D,L-lactide) block copolymer micelles with Modulated Surface Charge," *Journal of Controlled Release*. (2001) 77:27-38.

Zhang et al., "Neointimal Hyperplasia Persists at Six Months after Siroli Mus-Eluting Stent Implantation in Diabetic Porcine," *Cardiovasc. Diabetol*. (2007) 6:16:1-7.

Altmann (Epothilone B and its analogs—a new family of anticancer agents, *Mini Rev Med Chem*. (2003) 3(2):149-158; Abstract Only [retrieved from Bentham Science, < URL: http://www.eurekaselect.com/80911/artcile>], 1 page.

Altmann (Epothilone B and its analogs—a new family of anticancer agents, *Mini Rev Med Chem*. (2003) 3(2):149-158; Abstract Only [retrieved from PUBMED, < URL: http://www.ncbi.nlm.nih.gov/pubmed/12570848>]), 1 page.

Dong et al., "In vitro and in vivo evaluation of methoxy polyethylene glycol-polylactide (MPEG-PLA) nanoparticles for small-molecule drug chemotherapy," (2007) *Biomaterials*. 28:4154-4160.

Eurasian Official Action for EA 201170038, dated Aug. 12, 2013.

Eurasian Official Action for EA 201170040, dated Jun. 29, 2012.

Eurasian Search Report for Application No. EA 201100765, dated Aug. 2, 2013.

Eurasian Search Report for Application No. EA 201290497, dated Jan. 15, 2013.

European Examination Report for EP 09794913.5, dated Jul. 16, 2012.

Extended European Search Report for EP 09794913.5 mailed Jul. 4, 2013, 9 pages.

Extended European Search Report for EP 09794917.6 mailed Aug. 7, 2013, 8 pages.

Extended European Search Report for EP 10842554.7 mailed Jul. 10, 2013, 9 pages.

Extended European Search Report for EP 10842556.2 mailed Jul. 8, 2013, 9 pages.

Extended European Search Report for EP 10842557.0 mailed Jul. 8, 2013, 11 pages.

Extended European Search Report for EP 13162786.1 mailed Aug. 30, 2013, 7 pages.

Extended European Search Report for EP 13162789.5 mailed Aug. 30, 2013, 7 pages.

Gill et al., "Modulated Differential Scanning Calorimetry," J. Thermal Analysis. (1993) 40:931-939.

Gref et al., "Stealth Corona-Core Nanoparticles Surface Modified by Polyethylene Glycol (PEG): Influences of the Corona (PEG Chaing Length and Surface Density) and of the Core Composition on Phagocytic Uptake and Plasma Protein Adsorption," *Colloids and Surfaces B: Biointerfaces*, (2000) 301-313.

International Preliminary Report on Patentability for PCT/US2010/060575 dated Jun. 19, 2012, 11 pages.

Matsumoto et al., "Preparation of Nanoparticles consisted of poly(L-lactide)-poly(ethylene glycol)poly(L-lactide) and Their Evaluation In Vitro," International J. of Pharmaceutics. (1999) 185:93-101.

Merck (Betamethasone, Merck Index (Knovel, copyright 2006, 2012)), 3 pages.

Verrecchia et al., "Non-stealth (poly(lactic acid/albumin) ) and stealth (poly(lactic acid-polyethylene glycol) ) nanoparticles as injectable drug carriers," J. of Controlled Release. (1995) 36:49-61.

Allémann et al., "In vitro extended-release properties of drug-loaded poly(DL-Lactic Acid) nanoparticles produced by a salting-out procedure," *Pharmaceutical Research*. (1993) 10(12):1732-1737.

Allémann et al., "Preparation of aqueous polymeric nanodispersions by a reversible salting-out process: influence of process parameters on particle size," *Int. J. of Pharmaceutics*. (1992) 87:247-253.

Cayman Chemical, "Risperidone—Product Information" (https://www.caymanchem/pdfs/13629.pdf), 1 page, [Mar. 13, 2013].

Clinical Trials, "A Study of BIND-014 Given to Patients with Advanced or Mestastatic Cancer," [retrieved on May 9, 2014] Retrived from the internet <URL: http://clinicaltrials.gov/archive/NCT01300533/2013_04_30>, 4 pages.

Drug Bank (Canadian Institutes of Drug Research, Budesonide (DB01222) (2013) [Retrieved from internet <URL:http://www.drugbank.ca/drugs/DB01222 >], 9 pages.

International Search Report and Written Opinion for Application No. PCT/US2014/044617, dated Oct. 3, 2014 and mailed Oct. 3, 2014, 13 pages.

Notice of opposition for European Patent No. 2309990 dated Oct. 15, 2014, 5 pages.

Opposition Statement for European Patent No. 2309990 dated Oct. 15, 2014, 19 pages.

Song et al., "The effect of type of organic phase solvents on the particle size of poly(D,L-lactide-co-glycolide) nanoparticles," *Colloids and Surfaces A: Physicochem. Eng. Aspects*. (2006) 276:162-167.

Dong et al., "(Methoxy poly(ethylene glycol)-poly(lactide) (MPEG-PLA) nanoparticles for controlled delivery of anticancer drugs," (2004) *Biomaterials*. 25:2843-2849.

Dorati et al., "Polyethylenglycol-co-poly-D,L-lactide copolymer based microspheres: preparation, characterization and delivery of a model protein," *J Microencapsul*. (2008) 25(5):330-338.

Extended European Search Report for EP 14150948.9 mailed Jul. 8, 2014, 8 pages.

Farokhzad et al., "Nanoparticle-aptamer bioconjugates for cancer targeting," *Expert Opin Drug Deliv*. (2006) 3(3):311-24.

Govender et al., "PLGA nanoparticles prepared by nanoprecipitation: drug loading and release studies of a water soluble drug," *J Control Release*. (1999) 57(2):171-85.

Gross, "Oral pH-modified release budesonide for treatment of inflammatory bowel disease, collagenous and lymphocytic colitis," *Expert Opin Pharmacother*. (2008) 9(7):1257-1265.

Jenning et al., "Characterisation of a novel solid lipid nanoparticle carrier system based on binary mixtures of liquid and solid lipids," *Int J Pharm*. (2000) 199(2):167-77.

Okassa et al., "Optimization of iron oxide nanoparticles encapsulation within poly(d,l-lactide-co-glycolide) sub-micron particles," *Eur J Pharm Biopharm*. (2007) 67(1):31-8.

(56) References Cited

OTHER PUBLICATIONS

Ren et al., "Preparation and characterization of magnetic PLA-PEG composite nanoparticles for drug targeting," *Reactive & Functional Polymers.* (2006) 66:944-951.

Stolnik et al., "(Polylactide-poly(ethylene glycol) micellar-like particles as potential drug carriers: production, colloidal properties and biological performance," (2001) *Journal Drug Targeting.* 9:361-378.

van Vlerken and Amiji, "Multi-functional polymeric nanoparticles for tumour-targeted drug delivery," *Expert Opin Drug Deliv.* (2006) 3(2):205-16.

Yoo et al., "Protein-fatty acid complex for enhanced loading and stability within biodegradable nanoparticles," *J Pharm Sci.* (2001) 90(2):194-201.

* cited by examiner

THERAPEUTIC POLYMERIC NANOPARTICLES COMPRISING VINCA ALKALOIDS AND METHODS OF MAKING AND USING SAME

RELATED APPLICATIONS

This application is a continuation of U.S. Ser. No. 12/485,467 filed Jun. 16, 2009 which claims priority to U.S. Ser. No. 61/061,760, filed Jun. 16, 2008; U.S. Ser. No. 61/105,916, filed Oct. 16, 2008, U.S. Ser. No. 61/106,777, filed Oct. 20, 2008; U.S. Ser. No. 61/169,514, filed Apr. 15, 2009; U.S. Ser. No. 61/175,209, filed May 4, 2009; U.S. Ser. No. 61/061,704, filed Jun. 16, 2008; U.S. Ser. No. 61/169,519, filed Apr. 15, 2009; U.S. Ser. No. 61/175,219 filed May 4, 2009; U.S. Ser. No. 61/061,697, filed Jun. 16, 2008; U.S. Ser. No. 61/088,159, filed Aug. 12, 2008; U.S. Ser. No. 61/169,541, filed Apr. 15, 2009; U.S. Ser. No. 61/175,226, filed May 4, 2009; U.S. Ser. No. 61/173784, filed Apr. 29, 2009; and U.S. Ser. No. 61/182,300, filed May 29, 2009; each of which is hereby incorporated by reference in their entirety.

This invention was made with United States Government support under Cooperative Agreement Number 70NANB7H7021 awarded by the National Institute of Standard and Technology (NIST). The United States Government has certain rights in the Invention.

BACKGROUND

Systems that deliver certain drugs to a patient (e.g., targeted to a particular tissue or cell type or targeted to a specific diseased tissue but not normal tissue), or that control release of drugs has long been recognized as beneficial. For example, therapeutics that include an active drug and that are capable of locating in a particular tissue or cell type e.g., a specific diseased tissue, may reduce the amount of the drug in tissues of the body that do not require treatment. This is particularly important when treating a condition such as cancer where it is desirable that a cytotoxic dose of the drug is delivered to cancer cells without killing the surrounding non-cancerous tissue. Further, such therapeutics may reduce the undesirable and sometimes life threatening side effects common in anti-cancer therapy. For example, nanoparticle therapeutics may, due the small size, evade recognition within the body allowing for targeted and controlled delivery while e.g., remaining stable for an effective amount of time.

Therapeutics that offer such therapy and/or controlled release and/or targeted therapy also must be able to deliver an effective amount of drug. It can be a challenge to prepare nanoparticle systems that have an appropriate amount of drug associated each nanoparticle, while keeping the size of the nanoparticles small enough to have advantageous delivery properties. For example, while it is desirable to load a nanoparticle with a high quantity of therapeutic agent, nanoparticle preparations that use a drug load that is too high will result in nanoparticles that are too large for practical therapeutic use. Further, it may be desirable for therapeutic nanoparticles to remain stable so as to e.g. substantially limit rapid or immediate release of the therapeutic agent.

Accordingly, a need exists for new nanoparticle formulations and methods of making such nanoparticles and compositions, that can deliver therapeutic levels of drugs to treat diseases such as cancer, while also reducing patient side effects.

SUMMARY

In one aspect, the invention provides therapeutic nanoparticle that includes an active agent or therapeutic agent, e.g. vinorelbine or vincristine or pharmaceutically acceptable salts thereof, and one, two, or three biocompatible polymers. For example, disclosed herein is a therapeutic nanoparticle comprising about 1 to about 20 weight percent of a therapeutic agent (for example vinorelbine or vincristine) and about 50 to about 99 weight percent of a biocompatible polymer, e.g., about 70 to about 99 weight percent of a biocompatible polymer. For example, the biocompatible polymer may be a diblock poly(lactic) acid-poly(ethylene)glycol copolymer (e.g. PLA-PEG) or a diblock (poly(lactic)-co-poly(glycolic) acid)-poly(ethylene)glycol copolymer (e.g. PLGA-PEG), or the biocompatible polymer may include two or more different biocompatible polymers, for example, the therapeutic nanoparticles can also include a homopolymer such as a poly (lactic) acid homopolymer. For example, a disclosed therapeutic nanoparticle may include about 1 to about 20 weight percent of a vinca alkaloid; and about 70 to about 99 weight percent biocompatible polymer, wherein the biocompatible polymer is selected from the group consisting of a) a diblock poly(lactic) acid-poly(ethylene)glycol copolymer, b) a diblock poly(lactic)-co-poly(glycolic) acid-poly(ethylene) glycol copolymer, c) a combination of a) and a poly(lactic) acid homopolymer; and d) a combination of b) and a poly (lactic) acid homopolymer.

The diameter of disclosed nanoparticles may be, for example, about 60 to about 120 nm, about 70 to about 120 nm, about 70 to about 140 nm or about 80 to about 130 nm.

Disclosed therapeutic nanoparticles may be stable for at least 5 days at 25° C., e.g. may remain stable over 5 days in vitro, e.g. in a sucrose solution. In another embodiment, disclosed particles may substantially immediately release less than about 2% or less than about 5%, less than about 7%, or even less than about 10% of the therapeutic agent (e.g. a vinca alkaloid) when placed in a phosphate buffer solution at room temperature, or at 37° C.

An exemplary therapeutic nanoparticle comprises about 1 to about 20 weight percent of a vinca alkaloid; and about 70 to about 99 weight percent biocompatible polymer, wherein the biocompatible polymer is selected from the group consisting of: a) a diblock poly(lactic) acid-poly(ethylene)glycol copolymer, b) a diblock poly(lactic)-co-poly(glycolic) acid-poly(ethylene)glycol copolymer, c) a combination of a) and a poly(lactic) acid homopolymer (e.g. includes a diblock poly (lactic) acid-poly(ethylene)glycol copolymer); and d) a combination of b) and a poly(lactic) acid homopolymer. Vinca alkaloids may include for example, vinorelbine or vincristine or a pharmaceutically acceptable salt thereof. For example, contemplated nanoparticles may include about 9 to about 16 weight percent of a vinca alkaloid compound. In another example, contemplated nanoparticles may include about 3 to about 9 weight percent of a vinca alkaloid compound. Disclosed therapeutic nanoparticles may include about 10 weight percent to about 20 weight percent vinorelbine or a pharmaceutically acceptable salt thereof. In addition, disclosed therapeutic nanoparticles may include about 3 weight percent to about 10 weight percent vincristine or a pharmaceutically acceptable salt thereof For example, disclosed nanoparticles may include a biocompatible polymer that is a diblock poly(lactic) acid-poly (ethylene)glycol copolymer. Diblock poly(lactic) acid-poly (ethylene)glycol copolymers that may form part of a disclosed nanoparticle may comprise poly(lactic acid) having a number average molecular weight of about 15 to 20 kDa and poly(ethylene)glycol having a number average molecular weight of about 4 to about 6 kDa. Diblock poly(lactic)-co-glycolic acid-poly(ethylene)glycol copolymer may include poly(lactic acid)-co-glycolic acid having a number average molecular weight of about 15 to 20 kDa, e.g., about 16 kDa and poly(ethylene)glycol having a number average molecular weight of about 4 to about 6 kDa, about 5 kDa. The poly (lactic)-co-poly(glycolic) acid portion of a contemplated diblock poly(lactic)-co-poly(glycolic) acid-poly(ethylene) glycol copolymer may have, in certain embodiments, about 50 mole percent glycolic acid and about 50 mole percent poly(lactic) acid.

An exemplary therapeutic nanoparticle may include about 40 to about 50 weight percent diblock poly(lactic)acid-poly (ethylene)glycol copolymer and about 40 to about 49 weight percent poly(lactic) acid homopolymer. Such poly(lactic) acid homopolymers may have e.g., a weight average molecular weight of about 8 to about 12 kDa, e.g., about 10 kDa.

In an optional embodiment, a disclosed nanoparticle may further include about 0.2 to about 10 weight percent of a diblock poly(lactic)-co-poly(glycolic) acid-poly(ethylene) glycol copolymer covalently bound to a targeting ligand.

An exemplary therapeutic nanoparticle is provided that includes about 10 to about 20 weight percent of vinorelbine or a pharmaceutically acceptable salt thereof or about 3 to about 10 weight percent of vincristine or a pharmaceutically acceptable salt thereof; a diblock polymer chosen from: poly(lactic) acid-poly(ethylene)glycol copolymer or a poly(lactic)-co-poly (glycolic) acid-poly(ethylene)glycol copolymer and a poly(lactic) acid homopolymer, for example a poly(lactic) acid homopolymer has a weight average molecular weight of about 10 kDa. Such a therapeutic nanoparticle may, in some embodiments, comprise about 40 to about 45 weight percent diblock polymer and about 40 to about 45 weight percent homopolymer. In some embodiments, disclosed nanoparticles may further include cetyl alcohol.

Also disclosed herein is a pharmaceutically acceptable composition comprising a plurality of disclosed therapeutic nanoparticles and a pharmaceutically acceptable excipient. Exemplary pharmaceutically acceptable excipients a sugar such as sucrose.

Also disclosed herein are methods of treating prostate, breast, or non-small cell lung cancer, comprising administering to a patient in need thereof an effective amount of a composition comprising a disclosed therapeutic nanoparticle In another embodiment, provided herein is plurality of therapeutic nanoparticles prepared by combining vinorelbine or vincristine or pharmaceutically acceptable salts thereof and a diblock poly(lactic)acid-polyethylene glycol or a diblock poly(lactic)acid-co-poly(glycolic)acid-polyethylene glycol polymer and optionally a homopolymer, with an organic solvent to form a first organic phase having about 10 to about 40% solids; combining the first organic phase with a first aqueous solution to form a second phase; emulsifying the second phase to form an emulsion phase; quenching the emulsion phase to form a quenched phase; adding a drug solubilizer to the quenched phase to form a solubilized phase of unencapsulated therapeutic agent; and filtering the solubilized phase to recover the nanoparticles, thereby forming a slurry of therapeutic nanoparticles each having about 3 to about 20 weight percent of vinorelbine or vincristine.

DETAILED DESCRIPTION

Figure 1:
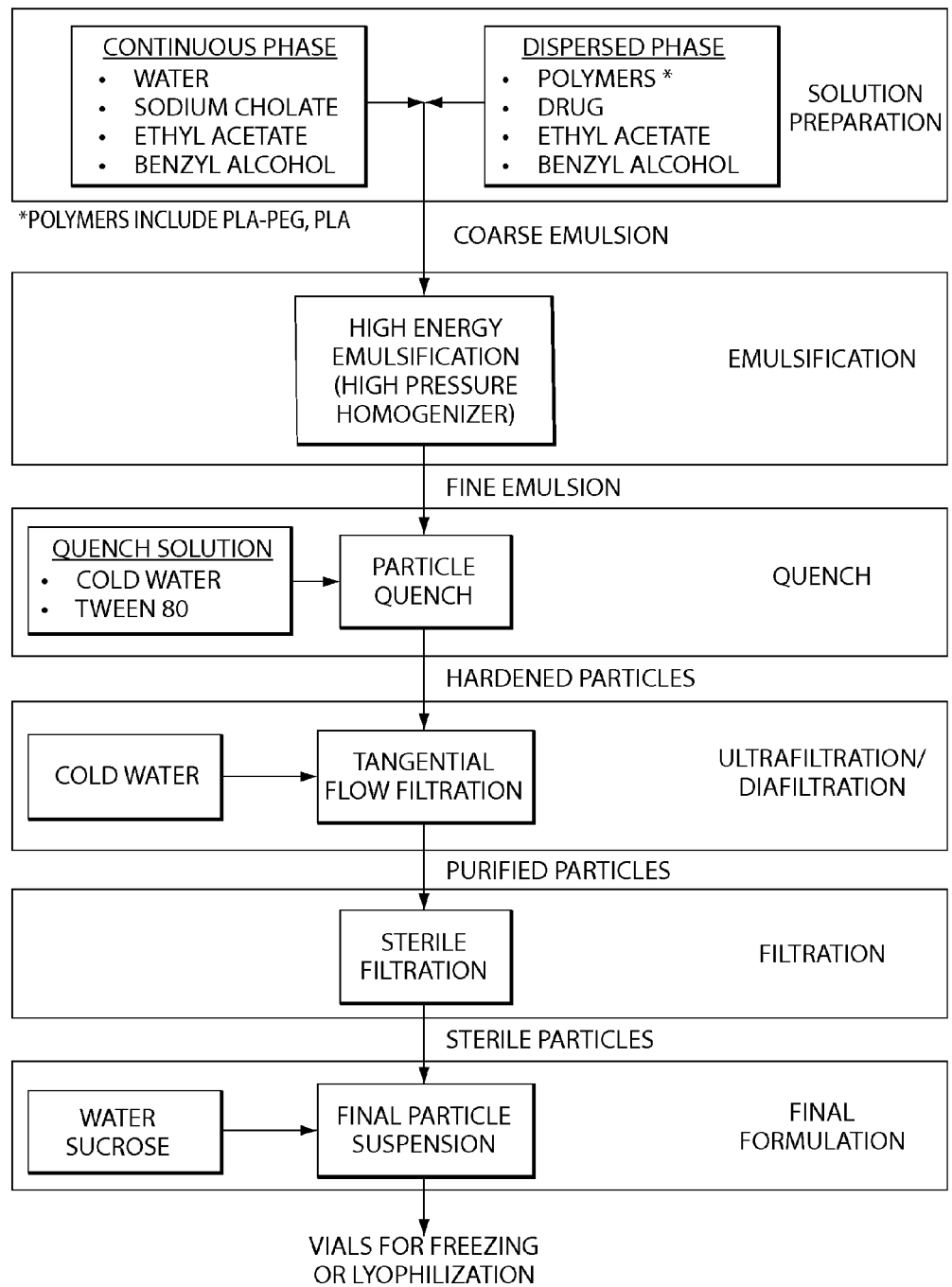
FIG. 1 is flow chart for an emulsion process for forming disclosed nanoparticle.

The present invention generally relates to polymeric nanoparticles that include an active or therapeutic agent or drug, and methods of making and using such therapeutic nanoparticles. In general, a "nanoparticle" refers to any particle having a diameter of less than 1000 nm, e.g. about 10 nm to about 200 nm. Disclosed therapeutic nanoparticles may include nanoparticles having a diameter of about 60 to about 120 nm, or about 70 to about 130 nm, or about 60 to about 140 nm, or about 70 nm to about 140 nm.

Disclosed nanoparticles may include about 0.2 to about 35 weight percent, about 3 to about 40 weight percent, about 5 to about 30 weight percent, about 1 to about 20 weight percent, about 10 to about 30 weight percent, about 15 to 25 weight percent, or even about 4 to about 25 weight percent of an active agent, such as antineoplastic agent, e.g. a vinca alkaloid agent (for example vinorelbine or vincristine or a pharmaceutically acceptable salt thereof).

Nanoparticles disclosed herein include one, two, three or more biocompatible and/or biodegradable polymers. For example, a contemplated nanoparticle may include about 60 to about 99 weight percent of one, two, three or more biocompatible polymers such as one or more co-polymers (e.g. a diblock polymer) that include a biodegradable polymer (for example poly(lactic)acid and polyethylene glycol, and optionally about 0 to about 50 weight percent of a homopolymer, e.g. biodegradable polymer such as poly(lactic) acid.

Polymers

In some embodiments, disclosed nanoparticles include a matrix of polymers. Disclosed nanoparticles may include one or more polymers, e.g. a diblock co-polymer and/or a monopolymer. Disclosed therapeutic nanoparticles may include a therapeutic agent that can be associated with the surface of, encapsulated within, surrounded by, and/or dispersed throughout a polymeric matrix.

A wide variety of polymers and methods for forming particles therefrom are known in the art of drug delivery. In some embodiments, the disclosure is directed toward nanoparticles with at least one polymer, for example, a first polymer that may be a co-polymer, e.g. a diblock co-polymer, and optionally a polymer that may be for example a homopolymer.

Any polymer can be used in accordance with the present invention. Polymers can be natural or unnatural (synthetic) polymers. Polymers can be homopolymers or copolymers comprising two or more monomers. In terms of sequence, copolymers can be random, block, or comprise a combination of random and block sequences. Contemplated polymers may be biocompatible and/or biodegradable.

The term "polymer," as used herein, is given its ordinary meaning as used in the art, i.e., a molecular structure comprising one or more repeat units (monomers), connected by covalent bonds. The repeat units may all be identical, or in some cases, there may be more than one type of repeat unit present within the polymer. In some cases, the polymer can be biologically derived, i.e., a biopolymer. Non-limiting examples include peptides or proteins. In some cases, additional moieties may also be present in the polymer, for example biological moieties such as those described below. If more than one type of repeat unit is present within the polymer, then the polymer is said to be a "copolymer." It is to be understood that in any embodiment employing a polymer, the polymer being employed may be a copolymer in some cases. The repeat units forming the copolymer may be arranged in any fashion. For example, the repeat units may be arranged in a random order, in an alternating order, or as a block copolymer, i.e., comprising one or more regions each comprising a first repeat unit (e.g., a first block), and one or more regions each comprising a second repeat unit (e.g., a second block), etc. Block copolymers may have two (a diblock copolymer), three (a triblock copolymer), or more numbers of distinct blocks.

Disclosed particles can include copolymers, which, in some embodiments, describes two or more polymers (such as those described herein) that have been associated with each other, usually by covalent bonding of the two or more polymers together. Thus, a copolymer may comprise a first polymer and a second polymer, which have been conjugated together to form a block copolymer where the first polymer can be a first block of the block copolymer and the second polymer can be a second block of the block copolymer. Of course, those of ordinary skill in the art will understand that a block copolymer may, in some cases, contain multiple blocks of polymer, and that a "block copolymer," as used herein, is not limited to only block copolymers having only a single first block and a single second block. For instance, a block copolymer may comprise a first block comprising a first polymer, a second block comprising a second polymer, and a third block comprising a third polymer or the first polymer, etc. In some cases, block copolymers can contain any number of first blocks of a first polymer and second blocks of a second polymer (and in certain cases, third blocks, fourth blocks, etc.). In addition, it should be noted that block copolymers can also be formed, in some instances, from other block copolymers. For example, a first block copolymer may be conjugated to another polymer (which may be a homopolymer, a biopolymer, another block copolymer, etc.), to form a new block copolymer containing multiple types of blocks, and/or to other moieties (e.g., to non-polymeric moieties).

In some embodiments, the polymer (e.g., copolymer, e.g., block copolymer) can be amphiphilic, i.e., having a hydrophilic portion and a hydrophobic portion, or a relatively hydrophilic portion and a relatively hydrophobic portion. A hydrophilic polymer can be one generally that attracts water and a hydrophobic polymer can be one that generally repels water. A hydrophilic or a hydrophobic polymer can be identified, for example, by preparing a sample of the polymer and measuring its contact angle with water (typically, the polymer will have a contact angle of less than 60°, while a hydrophobic polymer will have a contact angle of greater than about) 60°. In some cases, the hydrophilicity of two or more polymers may be measured relative to each other, i.e., a first polymer may be more hydrophilic than a second polymer. For instance, the first polymer may have a smaller contact angle than the second polymer.

In one set of embodiments, a polymer (e.g., copolymer, e.g., block copolymer) contemplated herein includes a biocompatible polymer, i.e., the polymer that does not typically induce an adverse response when inserted or injected into a living subject, for example, without significant inflammation and/or acute rejection of the polymer by the immune system, for instance, via a T-cell response. Accordingly, the therapeutic particles contemplated herein can be non-immunogenic. The term non-immunogenic as used herein refers to endogenous growth factor in its native state which normally elicits no, or only minimal levels of, circulating antibodies, T-cells, or reactive immune cells, and which normally does not elicit in the individual an immune response against itself.

Biocompatibility typically refers to the acute rejection of material by at least a portion of the immune system, i.e., a nonbiocompatible material implanted into a subject provokes an immune response in the subject that can be severe enough such that the rejection of the material by the immune system cannot be adequately controlled, and often is of a degree such that the material must be removed from the subject. One simple test to determine biocompatibility can be to expose a polymer to cells in vitro; biocompatible polymers are polymers that typically will not result in significant cell death at moderate concentrations, e.g., at concentrations of 50 micrograms/$10^6$ cells. For instance, a biocompatible polymer may cause less than about 20% cell death when exposed to cells such as fibroblasts or epithelial cells, even if phagocytosed or otherwise uptaken by such cells. Non-limiting examples of biocompatible polymers that may be useful in various embodiments of the present invention include polydioxanone (PDO), polyhydroxyalkanoate, polyhydroxybutyrate, poly (glycerol sebacate), polyglycolide, polylactide, PLGA, polycaprolactone, or copolymers or derivatives including these and/or other polymers.

In certain embodiments, contemplated biocompatible polymers may be biodegradable, i.e., the polymer is able to degrade, chemically and/or biologically, within a physiological environment, such as within the body. As used herein, "biodegradable" polymers are those that, when introduced into cells, are broken down by the cellular machinery (biologically degradable) and/or by a chemical process, such as hydrolysis, (chemically degradable) into components that the cells can either reuse or dispose of without significant toxic effect on the cells. In one embodiment, the biodegradable polymer and their degradation byproducts can be biocompatible.

For instance, a contemplated polymer may be one that hydrolyzes spontaneously upon exposure to water (e.g., within a subject), the polymer may degrade upon exposure to heat (e.g., at temperatures of about 37° C.). Degradation of a polymer may occur at varying rates, depending on the polymer or copolymer used. For example, the half-life of the polymer (the time at which 50% of the polymer can be degraded into monomers and/or other nonpolymeric moieties) may be on the order of days, weeks, months, or years, depending on the polymer. The polymers may be biologically degraded, e.g., by enzymatic activity or cellular machinery, in some cases, for example, through exposure to a lysozyme (e.g., having relatively low pH). In some cases, the polymers may be broken down into monomers and/or other nonpolymeric moieties that cells can either reuse or dispose of without significant toxic effect on the cells (for example, polylactide may be hydrolyzed to form lactic acid, polyglycolide may be hydrolyzed to form glycolic acid, etc.).

In some embodiments, polymers may be polyesters, including copolymers comprising lactic acid and glycolic acid units, such as poly(lactic acid-co-glycolic acid) and poly (lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; PEGylated polymers and copolymers of lactide and glycolide (e.g., PEGylated PLA, PEGylated PGA, PEGylated PLGA, and derivatives thereof. In some embodiments, polyesters include, for example, polyanhydrides, poly(ortho ester) PEGylated poly(ortho ester), poly(caprolactone), PEGylated poly(caprolactone), polylysine, PEGylated polylysine, poly(ethylene imine), PEGylated poly(ethylene imine), poly(L-lactide-co-L-lysine), poly(serine ester), poly (4-hydroxy-L-proline ester), poly[α-(4-aminobutyl)-L-glycolic acid], and derivatives thereof.

In some embodiments, a polymer may be PLGA. PLGA is a biocompatible and biodegradable co-polymer of lactic acid and glycolic acid, and various forms of PLGA can be characterized by the ratio of lactic acid:glycolic acid. Lactic acid can be L-lactic acid, D-lactic acid, or D,L-lactic acid. The degradation rate of PLGA can be adjusted by altering the lactic acid-glycolic acid ratio. In some embodiments, PLGA to be used in accordance with the present invention can be characterized by a lactic acid:glycolic acid molar ratio of approximately 85:15, approximately 75:25, approximately 60:40, approximately 50:50, approximately 40:60, approximately 25:75, or approximately 15:85.

In some embodiments, the ratio of lactic acid to glycolic acid monomers in the polymer of the particle (e.g., the PLGA block copolymer or PLGA-PEG block copolymer), may be selected to optimize for various parameters such as water uptake, therapeutic agent release and/or polymer degradation kinetics can be optimized.

In some embodiments, polymers may be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, amino alkyl methacrylate copolymer, poly(acrylic acid), poly(methacrylic acid), methacrylic acid alkylamide copolymer, poly(methyl methacrylate), poly(methacrylic acid polyacrylamide, amino alkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

In some embodiments, polymers can be cationic polymers. In general, cationic polymers are able to condense and/or protect negatively charged strands of nucleic acids (e.g. DNA, RNA, or derivatives thereof). Amine-containing polymers such as poly(lysine), polyethylene imine (PEI), and poly(amidoamine) dendrimers are contemplated for use, in some embodiments, in a disclosed particle.

In some embodiments, polymers can be degradable polyesters bearing cationic side chains. Examples of these polyesters include poly(L-lactide-co-L-lysine), poly(serine ester), and poly(4-hydroxy-L-proline ester). A polymer (e.g., copolymer, e.g., block copolymer) containing poly(ethylene glycol) repeat units can also be referred to as a "PEGylated" polymer. Such polymers can control inflammation and/or immunogenicity (i.e., the ability to provoke an immune response) and/or lower the rate of clearance from the circulatory system via the reticuloendothelial system (RES), due to the presence of the poly(ethylene glycol) groups.

PEGylation may also be used, in some cases, to decrease charge interaction between a polymer and a biological moiety, e.g., by creating a hydrophilic layer on the surface of the polymer, which may shield the polymer from interacting with the biological moiety. In some cases, the addition of poly (ethylene glycol) repeat units may increase plasma half-life of the polymer (e.g., copolymer, e.g., block copolymer), for instance, by decreasing the uptake of the polymer by the phagocytic system while decreasing transfection/uptake efficiency by cells. Those of ordinary skill in the art will know of methods and techniques for PEGylating a polymer, for example, by using EDC (1-ethyl-3-(3-dimethylaminopropyl) carbodiimide hydrochloride) and NHS (N-hydroxysuccinimide) to react a polymer to a PEG group terminating in an amine, by ring opening polymerization techniques (ROMP), or the like.

It is contemplated that PEG may include a terminal end group, for example, when PEG is not conjugated to a ligand. For example, PEG may terminate in a hydroxyl, a methoxy or other alkoxyl group, a methyl or other alkyl group, an aryl group, a carboxylic acid, an amine, an amide, an acetyl group, a guanidino group, or an imidazole. Other contemplated end groups include azide, alkyne, maleimide, aldehyde, hydrazide, hydroxylamine, alkoxyamine, or thiol moieties.

Particles disclosed herein may or may not contain PEG. In addition, certain embodiments can be directed towards copolymers containing poly(ester-ether)s, e.g., polymers having repeat units joined by ester bonds (e.g., R—C(O)—O—R' bonds) and ether bonds (e.g., R—O—R' bonds). In some embodiments of the invention, a biodegradable polymer, such as a hydrolyzable polymer, containing carboxylic acid groups, may be conjugated with poly(ethylene glycol) repeat units to form a poly(ester-ether).

In one embodiment, the molecular weight of the polymers can be optimized for effective treatment as disclosed herein. For example, the molecular weight of a polymer may influence particle degradation rate (such as when the molecular weight of a biodegradable polymer can be adjusted), solubility, water uptake, and drug release kinetics. For example, the molecular weight of the polymer can be adjusted such that the particle biodegrades in the subject being treated within a reasonable period of time (ranging from a few hours to 1-2 weeks, 3-4 weeks, 5-6 weeks, 7-8 weeks, etc.). A disclosed particle can for example comprise a copolymer of PEG and PLGA, the PEG can have a molecular weight of 1,000-20,000 Da, e.g., 5,000-20,000 Da, e.g., 10,000-20,000 Da, and the PLGA can have a molecular weight of 5,000-100,000 Da, e.g., 20,000-70,000 Da, e.g., 20,000-50,000 Da.

For example, disclosed here is an exemplary therapeutic nanoparticle that includes about 10 to about 99 weight percent poly(lactic) acid-poly(ethylene)glycol copolymer or poly(lactic)-co-poly(glycolic) acid-poly(ethylene)glycol copolymer, or about 20 to about 80 weight percent, about 40 to about 80 weight percent, or about 30 to about 50 weight percent, or about 70 to about 90 weight percent poly(lactic) acid-poly(ethylene)glycol copolymer or poly(lactic)-co-poly (glycolic) acid-poly(ethylene)glycol copolymer. Exemplary poly(lactic) acid-poly(ethylene)glycol copolymers can include a number average molecular weight of about 15 to about 20 kDa, or about 10 to about 25 kDa of poly(lactic) acid and a number average molecular weight of about 4 to about 6, or about 2kDa to about 10 kDa of poly(ethylene)glycol.

Disclosed nanoparticles may optionally include about 1 to about 50 weight percent poly(lactic) acid or poly(lactic) acidco-poly(glycolic) acid (which does not include PEG, e.g a homopolymer of PLA), or may optionally include about 1 to about 50 weight percent, or about 10 to about 50 weight percent or about 30 to about 50 weight percent poly(lactic) acid or poly(lactic) acid-co-poly(glycolic) acid. For example, poly(lactic) or poly(lactic)-co-poly(glycolic) acid may have a number average molecule weight of about 5 to about 15 kDa, or about 5 to about 12 kDa. Exemplary homopolymeric PLA may have a number average molecular weight of about 5 to about 10 kDa. Exemplary PLGA may have a number average molecular weight of about 8 to about 12 kDa.

In certain embodiments, disclosed polymers of may be conjugated to a lipid, e.g. "end-capped," for example, may include a lipid-terminated PEG. As described below, the lipid portion of the polymer can be used for self assembly with another polymer, facilitating the formation of a nanoparticle. For example, a hydrophilic polymer could be conjugated to a lipid that will self assemble with a hydrophobic polymer.

Exemplary lipids include fatty acids such as long chain (e.g., $C_8$-$C_{50}$), substituted or unsubstituted hydrocarbons. In some embodiments, a fatty acid group can be a $C_{10}$-$C_{20}$ fatty acid or salt thereof. In some embodiments, a fatty acid group can be a $C_{15}$-$C_{20}$ fatty acid or salt thereof. In some embodiments, a fatty acid can be unsaturated, monounsaturated, or polyunsaturated. For example, a fatty acid group can be one or more of butyric, caproic, caprylic, capric, lauric, myristic, palmitic, stearic, arachidic, behenic, or lignoceric acid. In some embodiments, a fatty acid group can be one or more of palmitoleic, oleic, vaccenic, linoleic, alpha-linolenic, gamma-linoleic, arachidonic, gadoleic, arachidonic, eicosapentaenoic, docosahexaenoic, or erucic acid.

In a particular embodiment, the lipid is of the Formula V:

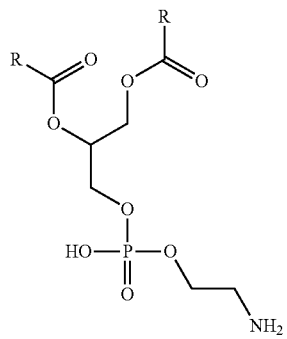

(V)

and salts thereof, wherein each R is, independently, $C_{1-30}$ alkyl. In one embodiment of Formula V, the lipid is 1,2 distearoyl-sn-glycero-3-phosphoethanolamine (DSPE), and salts thereof, e.g., the sodium salt.

In one embodiment, optional small molecule targeting moieties are bonded, e.g., covalently bonded, to the lipid component of the nanoparticle. For example, contemplated herein is also a nanoparticle comprising a therapeutic agent, a polymeric matrix comprising functionalized and non-functionalized polymers, a lipid, and a low-molecular weight targeting ligand, wherein the targeting ligand is bonded, e.g., covalently bonded, to the lipid component of the nanoparticle.

Targeting Moieties

Provided herein are nanoparticles that may include an optional targeting moiety, i.e., a moiety able to bind to or otherwise associate with a biological entity, for example, a membrane component, a cell surface receptor, prostate specific membrane antigen, or the like. A targeting moiety present on the surface of the particle may allow the particle to become localized at a particular targeting site, for instance, a tumor, a disease site, a tissue, an organ, a type of cell, etc. The drug or other payload may then, in some cases, be released from the particle and allowed to interact locally with the particular targeting site.

In one embodiment of the instant invention, the targeting moiety may be a low-molecular weight ligand, e.g., a low-molecular weight PSMA ligand. For example, a targeting portion may cause the particles to become localized to a tumor, a disease site, a tissue, an organ, a type of cell, etc. within the body of a subject, depending on the targeting moiety used. For example, a low-molecular weight PSMA ligand may become localized to prostate cancer cells. The subject may be a human or non-human animal. Examples of subjects include, but are not limited to, a mammal such as a dog, a cat, a horse, a donkey, a rabbit, a cow, a pig, a sheep, a goat, a rat, a mouse, a guinea pig, a hamster, a primate, a human or the like.

Contemplated targeting moieties include small molecules. In certain embodiments, the term "small molecule" refers to organic compounds, whether naturally-occurring or artificially created (e.g., via chemical synthesis) that have relatively low molecular weight and that are not proteins, polypeptides, or nucleic acids. Small molecules typically have multiple carbon-carbon bonds. In certain embodiments, small molecules are less than about 2000 g/mol in size. In some embodiments, small molecules are less than about 1500 g/mol or less than about 1000 g/mol. In some embodiments, small molecules are less than about 800 g/mol or less than about 500 g/mol, for example about 100 g/mol to about 600 g/mol, or about 200 g/mol to about 500 g/mol. For example, a ligand may be a the low-molecular weight PSMA ligand such as

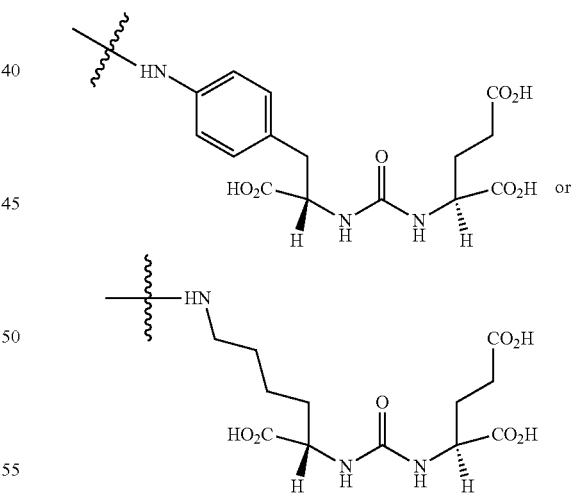

and enantiomers, stereoisomers, rotamers, tautomers, diastereomers, or racemates thereof.

In some embodiments, small molecule targeting moieties that may be used to target cells associated with prostate cancer tumors include PSMA peptidase inhibitors such as 2-PMPA, GPI5232, VA-033, phenylalkylphosphonamidates and/or analogs and derivatives thereof. In some embodiments, small molecule targeting moieties that may be used to target cells associated with prostate cancer tumors include thiol and indole thiol derivatives, such as 2-MPPA and 3-(2- mercaptoethyl)-1H-indole-2-carboxylic acid derivatives. In some embodiments, small molecule targeting moieties that may be used to target cells associated with prostate cancer tumors include hydroxamate derivatives. In some embodiments, small molecule targeting moieties that may be used to target cells associated with prostate cancer tumors include PBDA- and urea-based inhibitors, such as ZJ 43, ZJ 11, ZJ 17, ZJ 38 and/or and analogs and derivatives thereof, androgen receptor targeting agents (ARTAs), polyamines, such as putrescine, spermine, and spermidine, inhibitors of the enzyme glutamate carboxylase II (GCPII), also known as NAAG Peptidase or NAALADase.

In another embodiment of the instant invention, the targeting moiety can be a ligand that targets Her2, EGFR, or toll receptors. For example, contemplated the targeting moieties may include a nucleic acid, polypeptide, glycoprotein, carbohydrate, or lipid. For example, a targeting moiety can be a nucleic acid targeting moiety (e.g. an aptamer, e.g., the A10 aptamer) that binds to a cell type specific marker. In general, an aptamer is an oligonucleotide (e.g., DNA, RNA, or an analog or derivative thereof) that binds to a particular target, such as a polypeptide. In some embodiments, a targeting moiety may be a naturally occurring or synthetic ligand for a cell surface receptor, e.g., a growth factor, hormone, LDL, transferrin, etc. A targeting moiety can be an antibody, which term is intended to include antibody fragments, characteristic portions of antibodies, single chain targeting moieties can be identified, e.g., using procedures such as phage display. Targeting moieties may be a targeting peptide or targeting peptidomimetic has a length of up to about 50 residues. For example, targeting moieties may include the amino acid sequence AKERC, CREKA, ARYLQKLN or AXYLZZLN, wherein X and Z are variable amino acids, or conservative variants or peptidomimetics thereof. In particular embodiments, the targeting moiety is a peptide that includes the amino acid sequence AKERC, CREKA, ARYLQKLN or AXYLZZLN, wherein X and Z are variable amino acids, and has a length of less than 20, 50 or 100 residues. The CREKA (Cys Arg Glu Lys Ala) peptide or a peptidomimetic thereof peptide or the octapeptide AXYLZZLN are also contemplated as targeting moieties, as well as peptides, or conservative variants or peptidomimetics thereof, that binds or forms a complex with collagen IV, or the targets tissue basement membrane (e.g., the basement membrane of a blood vessel), can be used as a targeting moiety.

Exemplary targeting moieties include peptides that target ICAM (intercellular adhesion molecule, e.g. ICAM-1).

Targeting moieties disclosed herein are typically conjugated to a disclosed polymer or copolymer (e.g. PLA-PEG), and such a polymer conjugate may form part of a disclosed nanoparticle. For example, a disclosed therapeutic nanoparticle may optionally include about 0.2 to about 10 weight percent of a PLA-PEG or PLGA-PEG, wherein the PEG is functionalized with a targeting ligand. Contemplated therapeutic nanoparticles may include, for example, about 0.2 to about 10 mole percent PLA-PEG-ligand or poly(lactic) acid -co-poly (glycolic) acid-PEG-ligand. For example, PLA-PEG-ligand may include a PLA with a number average molecular weight of about 10 kDa to about 20 kDa and PEG with a number average molecular weight of about 4,000 to about 8,000 Da.

Nanoparticles

Disclosed nanoparticles may have a substantially spherical (i.e., the particles generally appear to be spherical), or non-spherical configuration. For instance, the particles, upon swelling or shrinkage, may adopt a non-spherical configuration. In some cases, the particles may include polymeric blends. For instance, a polymer blend may include a first co-polymer that includes polyethylene glycol and a second polymer.

Disclosed nanoparticles may have a characteristic dimension of less than about 1 micrometer, where the characteristic dimension of a particle is the diameter of a perfect sphere having the same volume as the particle. For example, the particle can have a characteristic dimension of the particle can be less than about 300 nm, less than about 200 nm, less than about 150 nm, less than about 100 nm, less than about 50 nm, less than about 30 nm, less than about 10 nm, less than about 3 nm, or less than about 1 nm in some cases. In particular embodiments, disclosed nanoparticles may have a diameter of about 70nm-200nm, or about 70 nm to about 180 nm, about 80 nm to about 130nm, about 80 nm to about 120 nm.

In one set of embodiments, the particles can have an interior and a surface, where the surface has a composition different from the interior, i.e., there may be at least one compound present in the interior but not present on the surface (or vice versa), and/or at least one compound is present in the interior and on the surface at differing concentrations. For example, in one embodiment, a compound, such as a targeting moiety (i.e., a low-molecular weight ligand) of a polymeric conjugate of the present invention, may be present in both the interior and the surface of the particle, but at a higher concentration on the surface than in the interior of the particle, although in some cases, the concentration in the interior of the particle may be essentially nonzero, i.e., there is a detectable amount of the compound present in the interior of the particle.

In some cases, the interior of the particle is more hydrophobic than the surface of the particle. For instance, the interior of the particle may be relatively hydrophobic with respect to the surface of the particle, and a drug or other payload may be hydrophobic, and readily associates with the relatively hydrophobic center of the particle. The drug or other payload can thus be contained within the interior of the particle, which can shelter it from the external environment surrounding the particle (or vice versa). For instance, a drug or other payload contained within a particle administered to a subject will be protected from a subject's body, and the body may also be substantially isolated from the drug for at least a period of time.

For example, disclosed herein is a therapeutic polymeric nanoparticle comprising a first non-functionalized polymer; an optional second non-functionalized polymer; an optional functionalized polymer comprising a targeting moiety; and a therapeutic agent. In a particular embodiment, the first non-functionalized polymer is PLA, PLGA, or PEG, or copolymers thereof, e.g. a diblock co-polymer PLA-PEG. For example, exemplary nanoparticle may have a PEG corona with a density of about 0.065 g/cm$^3$, or about 0.01 to about 0.10 g/cm$^3$.

Disclosed nanoparticles may be stable, for example in a solution that may contain a saccharide, for at least about 3 days, at least about 4 days or at least about 5 days at room temperature, or at 25° C.

In some embodiments, disclosed nanoparticles may also include a fatty alcohol, which may increase the rate of drug release. For example, disclosed nanoparticles may include a $C_8$-$C_{30}$ alcohol such as cetyl alcohol, octanol, stearyl alcohol, arachidyl alcohol, docosonal, or octasonal.

Nanoparticles may have controlled release properties, e.g., may be capable of delivering an amount of active agent to a patient, e.g., to specific site in a patient, over an extended period of time, e.g. over 1 day, 1 week, or more. In some embodiments, disclosed nanoparticles substantially immediately releases (e.g. over about 1 minute to about 30 minutes) less than about 2%, less than about 4%, less than about 5%, or less than about 10% of an active agent (e.g. a vinca alkaloid) agent, for example when places in a phosphate buffer solution at room temperature and/or at 37° C.

In one embodiment, the invention comprises a nanoparticle comprising 1) a polymeric matrix and 2) an amphiphilic compound or layer that surrounds or is dispersed within the polymeric matrix forming a continuous or discontinuous shell for the particle. An amphiphilic layer can reduce water penetration into the nanoparticle, thereby enhancing drug encapsulation efficiency and slowing drug release. Further, these amphipilic layer protected nanoparticles can provide therapeutic advantages by releasing the encapsulated drug and polymer at appropriate times.

As used herein, the term "amphiphilic" refers to a property where a molecule has both a polar portion and a non-polar portion. Often, an amphiphilic compound has a polar head attached to a long hydrophobic tail. In some embodiments, the polar portion is soluble in water, while the non-polar portion is insoluble in water. In addition, the polar portion may have either a formal positive charge, or a formal negative charge. Alternatively, the polar portion may have both a formal positive and a negative charge, and be a zwitterion or inner salt. Exemplary amphiphilic compound include, for example, one or a plurality of the following: naturally derived lipids, surfactants, or synthesized compounds with both hydrophilic and hydrophobic moieties.

Specific examples of amphiphilic compounds include, but are not limited to, phospholipids, such as 1,2 distearoyl-sn-glycero-3-phosphoethanolamine (DSPE), dipalmitoylphosphatidylcholine (DPPC), distearoylphosphatidylcholine (DSPC), diarachidoylphosphatidylcholine (DAPC), dibehenoylphosphatidylcholine (DBPC), ditricosanoylphosphatidylcholine (DTPC), and dilignoceroylphatidylcholine (DLPC), incorporated at a ratio of between 0.01-60 (weight lipid/w polymer), most preferably between 0.1-30 (weight lipid/w polymer). Phospholipids which may be used include, but are not limited to, phosphatidic acids, phosphatidyl cholines with both saturated and unsaturated lipids, phosphatidyl ethanolamines, phosphatidylglycerols, phosphatidylserines, phosphatidylinositols, lysophosphatidyl derivatives, cardiolipin, and β-acyl-y-alkyl phospholipids. Examples of phospholipids include, but are not limited to, phosphatidylcholines such as dioleoylphosphatidylcholine, dimyristoylphosphatidylcholine, dipentadecanoylphosphatidylcholine dilauroylphosphatidylcholine, dipalmitoylphosphatidylcholine (DPPC), distearoylphosphatidylcholine (DSPC), diarachidoylphosphatidylcholine (DAPC), dibehenoylphosphatidylcho-line (DBPC), ditricosanoylphosphatidylcholine (DTPC), dilignoceroylphatidylcholine (DLPC); and phosphatidylethanolamines such as dioleoylphosphatidylethanolamine or 1-hexadecyl-2-palmitoylglycerophos-phoethanolamine. Synthetic phospholipids with asymmetric acyl chains (e.g., with one acyl chain of 6 carbons and another acyl chain of 12 carbons) may also be used.

In a particular embodiment, an amphiphilic component may include lecithin, and/or in particular, phosphatidylcholine.

Preparation of Nanoparticles

Another aspect of the invention is directed to systems and methods of making disclosed nanoparticles. In some embodiments, using two or more different polymers (e.g., a copolymer such as a diblock copolymer and a homopolymer) properties of particles may be controlled.

In a particular embodiment, the methods described herein form nanoparticles that have a high amount of encapsulated therapeutic agent, for example, may include about 1 to about 40 weight percent, or about 1 to about 30 weight percent, e.g. about 10 to about 25 weight percent or about 5 to about 20 weight percent therapeutic agent.

Figure 2A:
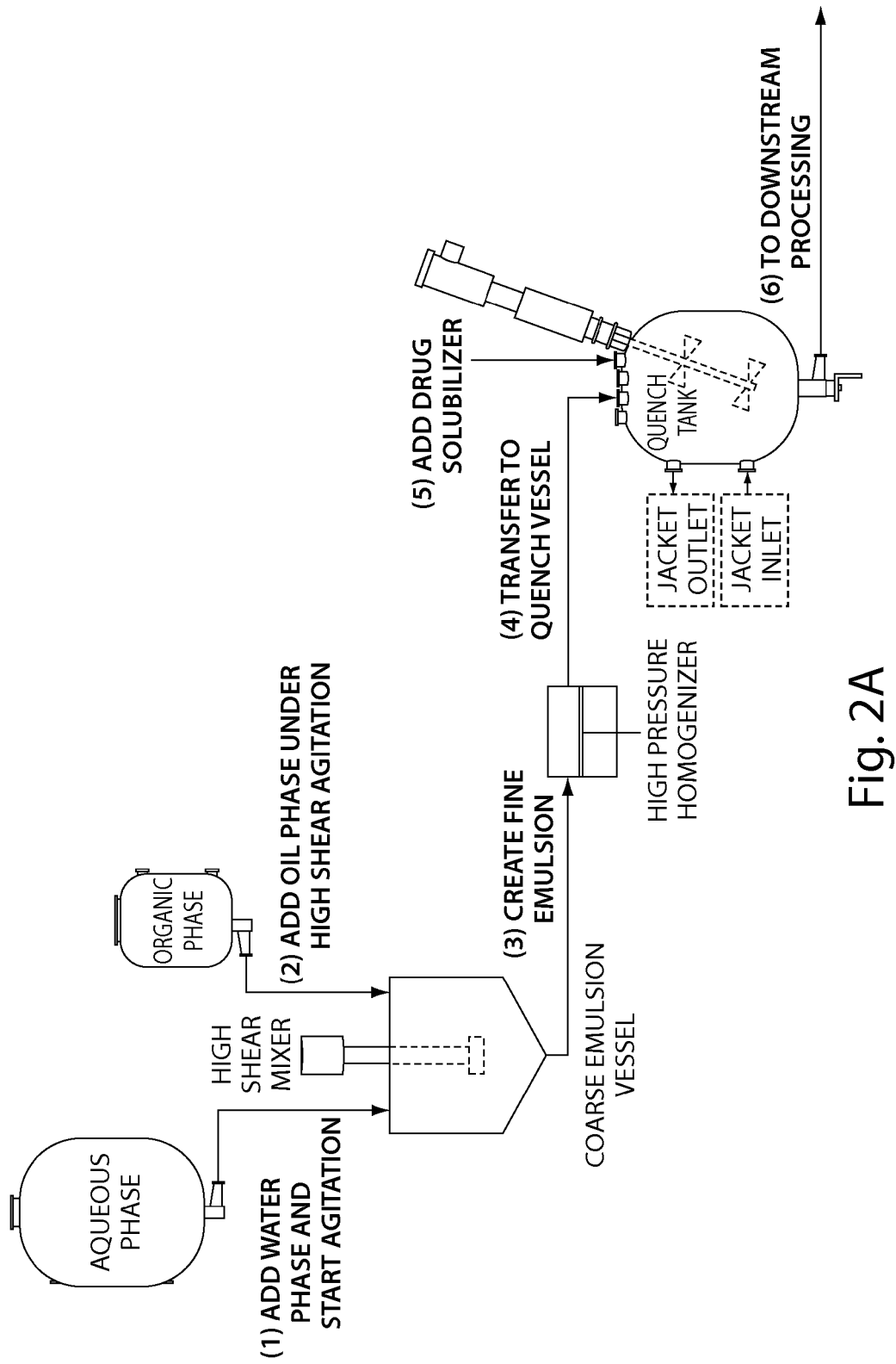
FIGS. 2A and 2B are flow diagrams for a disclosed emulsion processes.
Figure 2B:
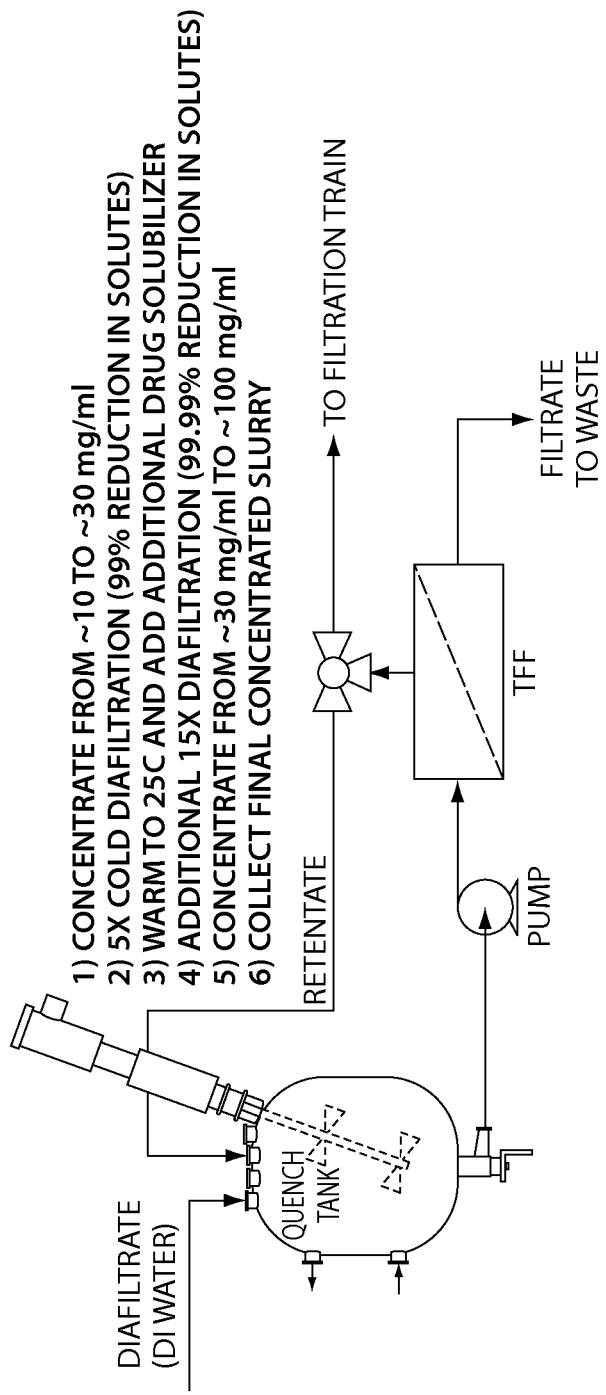

In an embodiment, a nanoemulsion process is provided, such as the process represented in FIGS. 1 and 2. For example, a therapeutic agent, a first polymer (for example, PLA-PEG or PLGA-PEG) and a second polymer (e.g. (PL(G)A or PLA), with an organic solution to form a first organic phase. Such first phase may include about 5 to about 50% weight solids, e.g about 5 to about 40% solids, or about 10 to about 30% solids, e.g. about 10%, 15%, 20% solids. The first organic phase may be combined with a first aqueous solution to form a second phase. The organic solution can include, for example, acetonitrile, tetrahydrofuran, ethyl acetate, isopropyl alcohol, isopropyl acetate, dimethylformamide, methylene chloride, dichloromethane, chloroform, acetone, benzyl alcohol, Tween 80, Span 80,or the like, and combinations thereof. In an embodiment, the organic phase may include benzyl alcohol, ethyl acetate, and combinations thereof. The second phase can be between about 1 and 50 weight %, e.g., 5-40 weight %, solids. The aqueous solution can be water, optionally in combination with one or more of sodium cholate, ethyl acetate, and benzyl alcohol.

For example, the oil or organic phase may use solvent that is only partially miscible with the nonsolvent (water). Therefore, when mixed at a low enough ratio and/or when using water pre-saturated with the organic solvents, the oil phase remains liquid. The oil phase may bee emulsified into an aqueous solution and, as liquid droplets, sheared into nanoparticles using, for example, high energy dispersion systems, such as homogenizers or sonicators. The aqueous portion of the emulsion, otherwise known as the "water phase", may be surfactant solution consisting of sodium cholate and pre-saturated with ethyl acetate and benzyl alcohol.

Emulsifying the second phase to form an emulsion phase may be performed in one or two emulsification steps. For example, a primary emulsion may be prepared, and then emulsified to form a fine emulsion. The primary emulsion can be formed, for example, using simple mixing, a high pressure homogenizer, probe sonicator, stir bar, or a rotor stator homogenizer. The primary emulsion may be formed into a fine emulsion through the use of e.g. probe sonicator or a high pressure homogenizer, e.g. by using 1, 2, 3 or more passes through a homogenizer. For example, when a high pressure homogenizer is used, the pressure used may be about 4000 to about 8000 psi, or about 4000 to about 5000 psi, e.g. 4000 or 5000 psi.

Either solvent evaporation or dilution may be needed to complete the extraction of the solvent and solidify the particles. For better control over the kinetics of extraction and a more scalable process, a solvent dilution via aqueous quench may be used. For example, the emulsion can be diluted into cold water to a concentration sufficient to dissolve all of the organic solvent to form a quenched phase. Quenching may be performed at least partially at a temperature of about 5° C. or less. For example, water used in the quenching may be at a temperature that is less that room temperature (e.g. about 0 to about 10° C., or about 0 to about 5° C.).

In some embodiments, not all of the therapeutic agent is encapsulated in the particles at this stage, and a drug solubilizer is added to the quenched phase to form a solubilized phase. The drug solubilizer may be for example, Tween 80, Tween 20, polyvinyl pyrrolidone, cyclodextran, sodium dodecyl sulfate, or sodium cholate. For example, Tween-80 may added to the quenched nanoparticle suspension to solubilize the free drug and prevent the formation of drug crystals. In some embodiments, a ratio of drug solubilizer to therapeutic agent is about 100:1 to about 10:1.

The solubilized phase may be filtered to recover the nanoparticles. For example, ultrafiltration membranes may be used to concentrate the nanoparticle suspension and substantially eliminate organic solvent, free drug, and other processing aids (surfactants). Exemplary filtration may be performed using a tangential flow filtration system. For example, by using a membrane with a pore size suitable to retain nanoparticles while allowing solutes, micelles, and organic solvent to pass, nanoparticles can be selectively separated. Exemplary membranes with molecular weight cut-offs of about 300-500 kDa (~5-25 nm) may be used.

Diafiltration may be performed using a constant volume approach, meaning the diafiltrate (cold deionized water, e.g. about 0° C. to about 5° C., or 0 to about 10° C.) may added to the feed suspension at the same rate as the filtrate is removed from the suspension. In some embodiments, filtering may include a first filtering using a first temperature of about 0° C. to about 5° C., or 0° C. to about 10° C., and a second temperature of about 20° C. to about 30° C., or 15° C. to about 35° C. For example, filtering may include processing about 1 to about 6 diavolumes at about 0° C. to about 5° C., and processing at least one diavolume (e.g. about 1 to about 3 or about 1-2 diavolumes) at about 20° C. to about 30° C.

After purifying and concentrating the nanoparticle suspension, the particles may be passed through one, two or more sterilizing and/or depth filters, for example, using ~0.2 µm depth pre-filter.

In exemplary embodiment of preparing nanoparticles, an organic phase is formed composed of a mixture of a therapeutic agent, e.g., vinorelbine or vincristine, and polymer (homopolymer, and co-polymer). The organic phase may be mixed with an aqueous phase at approximately a 1:5 ratio (oil phase:aqueous phase) where the aqueous phase is composed of a surfactant and optionally dissolved solvent. A primary emulsion may then formed by the combination of the two phases under simple mixing or through the use of a rotor stator homogenizer. The primary emulsion is then formed into a fine emulsion through the use of e.g. high pressure homogenizer. Such fine emulsion may then quenched by, e.g. addition to deionized water under mixing. An exemplary quench:emulsion ratio may be about approximately 8.5:1. A solution of Tween (e.g., Tween 80) can then be added to the quench to achieve e.g. approximately 2% Tween overall, which may serves to dissolve free, unencapsulated drug. Formed nanoparticles may then be isolated through either centrifugation or ultrafiltration/diafiltration.

Therapeutic Agents

According to the present invention, any agents including, for example, therapeutic agents (e.g. anti-cancer agents), diagnostic agents (e.g. contrast agents; radionuclides; and fluorescent, luminescent, and magnetic moieties), prophylactic agents (e.g. vaccines), and/or nutraceutical agents (e.g. vitamins, minerals, etc.) may be delivered by the disclosed nanoparticles. Exemplary agents to be delivered in accordance with the present invention include, but are not limited to, small molecules (e.g. cytotoxic agents), nucleic acids (e.g., siRNA, RNAi, and microRNA agents), proteins (e.g. antibodies), peptides, lipids, carbohydrates, hormones, metals, radioactive elements and compounds, drugs, vaccines, immunological agents, etc., and/or combinations thereof. In some embodiments, the agent to be delivered is an agent useful in the treatment of cancer (e.g., an anti-neoplastic agent).

In a particular embodiment, the drug may be released in a controlled release manner from the particle and allowed to interact locally with the particular patient site (e.g., a tumor). The term "controlled release" is generally meant to encompass release of a substance (e.g., a drug) at a selected site or otherwise controllable in rate, interval, and/or amount. Controlled release encompasses, but is not necessarily limited to, substantially continuous delivery, patterned delivery (e.g., intermittent delivery over a period of time that is interrupted by regular or irregular time intervals), and delivery of a bolus of a selected substance (e.g., as a predetermined, discrete amount if a substance over a relatively short period of time (e.g., a few seconds or minutes)).

The active agent or drug may be a therapeutic agent such as sirolimus, temsirolimus, everolimus, vincristine, a taxane, or a diterpene derivative such as paclitaxel (or its derivatives such as DHA-paclitaxel or PG-paxlitaxel) or docetaxel. In another embodiment, the active agent or drug may be a vinca alkaloid such as vinorelbine, vinblastine, vincristine, or vindesine.

Pharmaceutical Formulations

Nanoparticles disclosed herein may be combined with pharmaceutical acceptable carriers to form a pharmaceutical composition. As would be appreciated by one of skill in this art, the carriers may be chosen based on the route of administration as described below, the location of the target issue, the drug being delivered, the time course of delivery of the drug, etc.

The pharmaceutical compositions and particles disclosed herein can be administered to a patient by any means known in the art including oral and parenteral routes. The term "patient," as used herein, refers to humans as well as non-humans, including, for example, mammals, birds, reptiles, amphibians, and fish. For instance, the non-humans may be mammals (e.g., a rodent, a mouse, a rat, a rabbit, a monkey, a dog, a cat, a primate, or a pig). In certain embodiments parenteral routes are desirable since they avoid contact with the digestive enzymes that are found in the alimentary canal. According to such embodiments, inventive compositions may be administered by injection (e.g., intravenous, subcutaneous or intramuscular, intraperitoneal injection), rectally, vaginally, topically (as by powders, creams, ointments, or drops), or by inhalation (as by sprays).

In a particular embodiment, disclosed nanoparticles may be administered to a subject in need thereof systemically, e.g., by IV infusion or injection.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension, or emulsion in a nontoxic parenterally acceptable diluent or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. In one embodiment, the inventive conjugate is suspended in a carrier fluid comprising 1% (w/v) sodium carboxymethyl cellulose and 0.1% (v/v) TWEEN™ 80. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

Solid dosage forms for oral administration include capsules, tablets, pills, powders, and granules. In such solid dosage forms, the encapsulated or unencapsulated conjugate is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may also comprise buffering agents.

Disclosed nanoparticles may be formulated in dosage unit form for ease of administration and uniformity of dosage. The expression "dosage unit form" as used herein refers to a physically discrete unit of nanoparticle appropriate for the patient to be treated. For any nanoparticle, the therapeutically effective dose can be estimated initially either in cell culture assays or in animal models, usually mice, rabbits, dogs, or pigs. An animal model may also used to achieve a desirable concentration range and route of administration. Such information can then be used to determine useful doses and routes for administration in humans. Therapeutic efficacy and toxicity of nanoparticles can be determined by standard pharmaceutical procedures in cell cultures or experimental animals, e.g., $ED_{50}$ (the dose is therapeutically effective in 50% of the population) and $LD_{50}$ (the dose is lethal to 50% of the population). The dose ratio of toxic to therapeutic effects is the therapeutic index, and it can be expressed as the ratio, $LD_{50}/ED_{50}$. Pharmaceutical compositions which exhibit large therapeutic indices may be useful in some embodiments. The data obtained from cell culture assays and animal studies can be used in formulating a range of dosage for human use.

In an exemplary embodiment, a pharmaceutical composition is disclosed that includes a plurality of nanoparticles each comprising a therapeutic agent; and a pharmaceutically acceptable excipient.

In some embodiments, a composition suitable for freezing is contemplated, including nanoparticles disclosed herein and a solution suitable for freezing, e.g., a sugar (e.g. sucrose) solution is added to a nanoparticle suspension. The sucrose may e.g., act as a cryoprotectant to prevent the particles from aggregating upon freezing. For example, provided herein is a nanoparticle formulation comprising a plurality of disclosed nanoparticles, sucrose and water; wherein, for example, the nanoparticles/sucrose/water are present at about 5-10%/10-15%/80-90% (w/w/w).

Methods of Treatment

In some embodiments, therapeutic particles disclosed herein may be used to treat, alleviate, ameliorate, relieve, delay onset of, inhibit progression of, reduce severity of, and/or reduce incidence of one or more symptoms or features of a disease, disorder, and/or condition. For example, disclosed therapeutic particles, that include e.g., vinorelbine or vincristine or pharmaceutically acceptable salts thereof may be used to treat cancers such as prostate, breast or lung cancer such as non-small cell lung cancer in a patient in need thereof. Also contemplated here are methods of treating prostate cancer, non-small cell lung cancer, colorectal carcinoma, and glioblastoma using disclosed nanoparticles.

Disclosed methods for the treatment of cancer (e.g. prostate or breast cancer) may comprise administering a therapeutically effective amount of the disclosed therapeutic particles to a subject in need thereof, in such amounts and for such time as is necessary to achieve the desired result. In certain embodiments of the present invention a "therapeutically effective amount" is that amount effective for treating, alleviating, ameliorating, relieving, delaying onset of, inhibiting progression of, reducing severity of, and/or reducing incidence of one or more symptoms or features of e.g. a cancer being treated.

Also provided herein are therapeutic protocols that include administering a therapeutically effective amount of an disclosed therapeutic particle to a healthy individual (i.e., a subject who does not display any symptoms of cancer and/or who has not been diagnosed with cancer). For example, healthy individuals may be "immunized" with an inventive targeted particle prior to development of cancer and/or onset of symptoms of cancer; at risk individuals (e.g., patients who have a family history of cancer; patients carrying one or more genetic mutations associated with development of cancer; patients having a genetic polymorphism associated with development of cancer; patients infected by a virus associated with development of cancer; patients with habits and/or lifestyles associated with development of cancer; etc.) can be treated substantially contemporaneously with (e.g., within 48 hours, within 24 hours, or within 12 hours of) the onset of symptoms of cancer. Of course individuals known to have cancer may receive inventive treatment at any time.

In other embodiments, disclosed nanoparticles may be used to inhibit the growth of cancer cells, e.g., prostate cancer cells. As used herein, the term "inhibits growth of cancer cells" or "inhibiting growth of cancer cells" refers to any slowing of the rate of cancer cell proliferation and/or migration, arrest of cancer cell proliferation and/or migration, or killing of cancer cells, such that the rate of cancer cell growth is reduced in comparison with the observed or predicted rate of growth of an untreated control cancer cell. The term "inhibits growth" can also refer to a reduction in size or disappearance of a cancer cell or tumor, as well as to a reduction in its metastatic potential. Preferably, such an inhibition at the cellular level may reduce the size, deter the growth, reduce the aggressiveness, or prevent or inhibit metastasis of a cancer in a patient. Those skilled in the art can readily determine, by any of a variety of suitable indicia, whether cancer cell growth is inhibited.

Inhibition of cancer cell growth may be evidenced, for example, by arrest of cancer cells in a particular phase of the cell cycle, e.g., arrest at the G2/M phase of the cell cycle. Inhibition of cancer cell growth can also be evidenced by direct or indirect measurement of cancer cell or tumor size. In human cancer patients, such measurements generally are made using well known imaging methods such as magnetic resonance imaging, computerized axial tomography and X-rays. Cancer cell growth can also be determined indirectly, such as by determining the levels of circulating carcinoembryonic antigen, prostate specific antigen or other cancer-specific antigens that are correlated with cancer cell growth Inhibition of cancer growth is also generally correlated with prolonged survival and/or increased health and well-being of the subject.

EXAMPLES

The invention now being generally described, it will be more readily understood by reference to the following examples which are included merely for purposes of illustration of certain aspects and embodiments of the present invention, and are not intended to limit the invention in any way.

Example 1

Preparation of PLA-PEG

The synthesis is accomplished by ring opening polymerization of d,l-lactide with α-hydroxy-ω-methoxypoly(ethylene glycol) as the macro-initiator, and performed at an elevated temperature using Tin (II) 2-Ethyl hexanoate as a catalyst, as shown below(PEG Mn≈5,000 Da; PLA Mn≈16,000 Da; PEGPLA $M_n$≈21,000 Da)

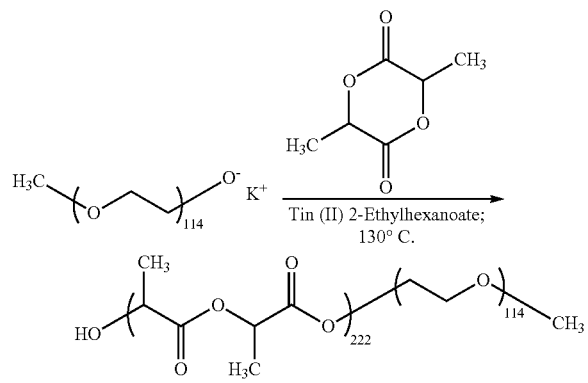

The polymer is purified by dissolving the polymer in dichloromethane, and precipitating it in a mixture of hexane and diethyl ether. The polymer recovered from this step shall be dried in an oven.

Example 2

Nanoparticle Preparation—Emulsion Process

An organic phase is formed composed of a mixture of vinorelbine and polymer (homopolymer, co-polymer, and co-polymer with ligand). The organic phase is mixed with an aqueous phase at approximately a 1:5 ratio (oil phase:aqueous phase) where the aqueous phase is composed of a surfactant and some dissolved solvent. In order to achieve high drug loading, about 30% solids in the organic phase is used.

The primary, coarse emulsion is formed by the combination of the two phases under simple mixing or through the use of a rotor stator homogenizer. The rotor/stator yielded a homogeneous milky solution, while the stir bar produced a visibly larger coarse emulsion. It was observed that the stir bar method resulted in significant oil phase droplets adhering to the side of the feed vessel, suggesting that while the coarse emulsion size is not a process parameter critical to quality, it should be made suitably fine in order to prevent yield loss or phase separation. Therefore the rotor stator is used as the standard method of coarse emulsion formation, although a high speed mixer may be suitable at a larger scale.

Figure 3:
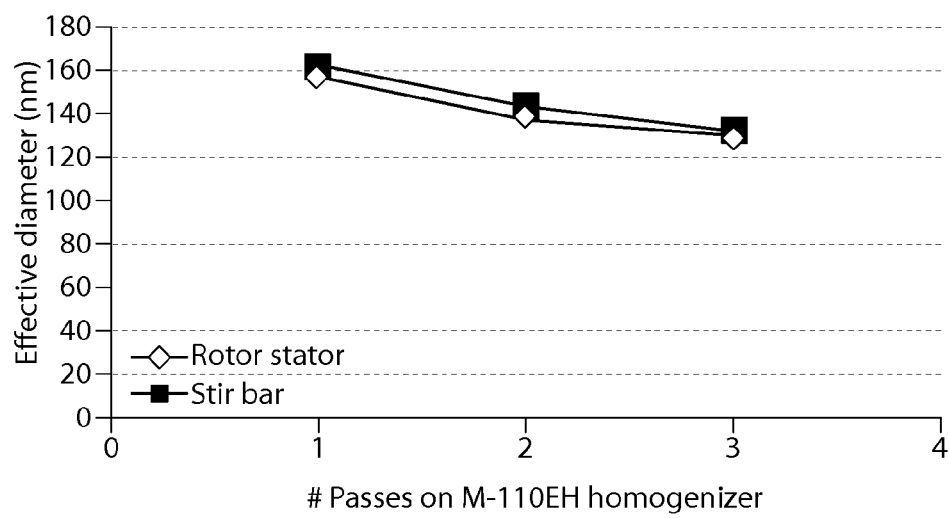
FIG. 3 depicts the effect of coarse emulsion preparation on quenched particle size. Placebo organic at 30% solids was used, emulsified at 5:1 W:O using standard aqueous phase (1% sodium cholate, 2% benzyl alcohol, 4% ethyl acetate).

The primary emulsion is then formed into a fine emulsion through the use of a high pressure homogenizer. The size of the coarse emulsion does not significantly affect the particle size after successive passes (1-3) through the homogenizer. M-110-EH (FIG. 3).

Figure 4:
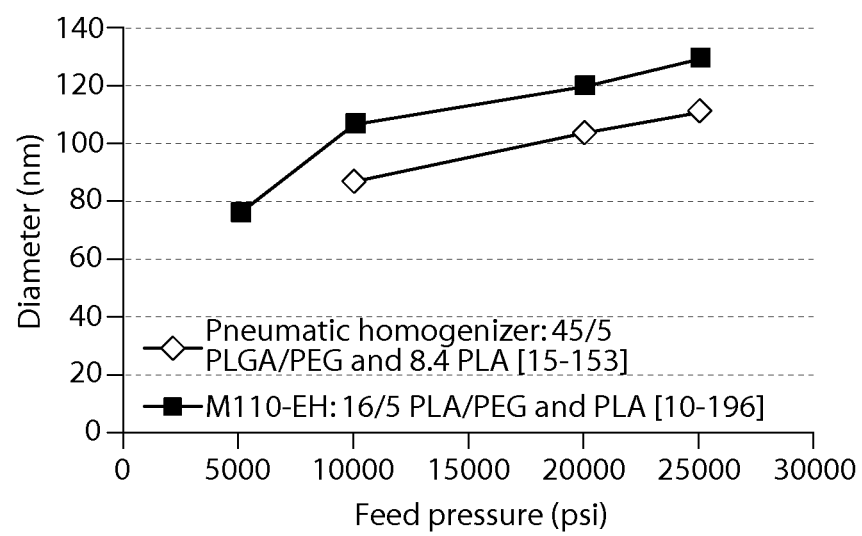
FIG. 4 depicts the effect of feed pressure on resultant particle size.

Homogenizer feed pressure was found to have a significant impact on resultant particle size. On both the pneumatic and electric M-110EH homogenizers, it was found that reducing the feed pressure also reduced the particle size (FIG. 4). Therefore the standard operating pressure used for the M-110EH is 4000-5000 psi per interaction chamber, which is the minimum processing pressure on the unit. The M-110EH also has the option of one or two interaction chambers. It comes standard with a restrictive Y-chamber, in series with a less restrictive 200 μm Z-chamber. It was found that the particle size was actually reduced when the Y-chamber was removed and replaced with a blank chamber. Furthermore, removing the Y-chamber significantly increases the flow rate of emulsion during processing.

Figure 5:
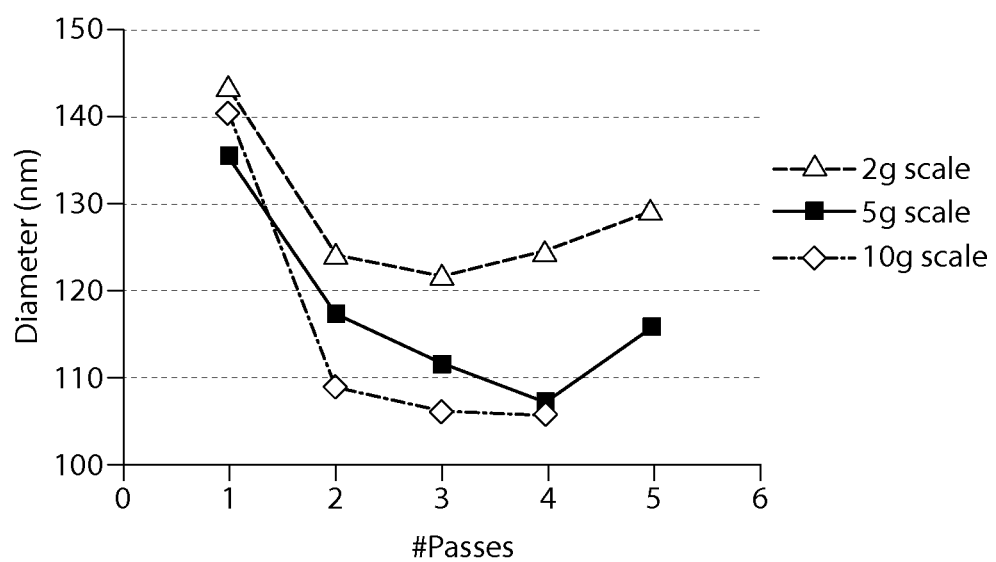
FIG. 5 depicts the particle size dependence on scale. Placebo organic phase consisted of 25.5% polymer stock of 50:50 16.5/5 PLA/PEG:8.2 PLA. Organic phase was emulsified 5:1 O:W with standard aqueous phase, and multiple discreet passes were performed, quenching a small portion of emulsion after each pass. The indicated scale represents the total solids of the formulation.

After 2-3 passes the particle size was not significantly reduced, and successive passes can even cause a particle size increase. The results are summarized in FIG. 5.

Figure 6:
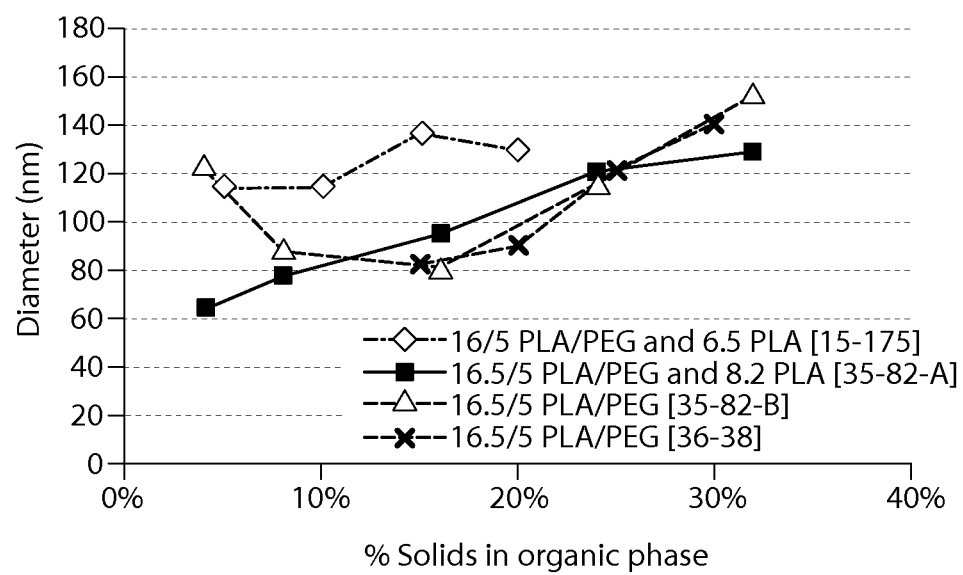
FIG. 6 depicts the effect of solids concentration on particle size.

The effect of scale on particle size showed surprising scale dependence. The trend shows that in the 2-10 g batch size range, larger batches produce smaller particles. It has been demonstrated that this scale dependence is eliminated when considering greater than 10 g scale batches. The amount of solids used in the oil phase was about 30%. FIG. 6 depicts the effect of solids concentration on particle size.

Table A summarizes the emulsification process parameters.

TABLE A

| Parameter | Value | Observation |
|---|---|---|
| Coarse emulsion formation | Rotor stator homogenizer | Coarse emulsion size does not affect final particle size, but large coarse emulsion can cause increased oil phase retention in feed vessel |
| Homogenizer feed pressure | 4000-5000 psi per chamber | Lower pressure reduces particle size |
| Interaction chamber(s) | 2 × 200 μm Z-chamber | 200 μm Z-chamber yields the smallest particle size, and allows for highest homogenizer throughput |
| Number of homogenizer passes | 2-3 passes | Studies have shown that the particle size is not significantly reduced after 2 discreet passes, and size can even increase with successive passes |
| Water phase [sodium cholate] | 0.1% | [Sodium cholate] can effectively alter particle size; value is optimized for given process and formulation |

TABLE A-continued

| Parameter | Value | Observation |
|---|---|---|
| W:O ratio | 5:1 | Lowest ratio without significant particle size increase is ~5:1 |
| [Solids] in oil phase | 30% | Increased process efficiency, increased drug encapsulation, workable viscosity |

The fine emulsion is then quenched by addition to deionized water at a given temperature under mixing. In the quench unit operation, the emulsion is added to a cold aqueous quench under agitation. This serves to extract a significant portion of the oil phase solvents, effectively hardening the nanoparticles for downstream filtration. Chilling the quench significantly improved drug encapsulation. The quench:emulsion ratio is approximately 5:1.

A solution of 35% (wt %) of Tween 80 is added to the quench to achieve approximately 2% Tween 80 overall. After the emulsion is quenched a solution of Tween-80 is added which acts as a drug solubilizer, allowing for effective removal of unencapsulated drug during filtration. Table B indicates each of the quench process parameters.

TABLE B

Summary quench process parameters.

| Parameter | Value | Observation |
|---|---|---|
| Initial quench temperature | <5° C. | Low temperature yields higher drug encapsulation |
| [Tween-80] solution | 35% | Highest concentration that can be prepared and readily disperses in quench |
| Tween-80:drug ratio | 25:1 | Minimum amount of Tween-80 required to effectively remove unencapsulated drug |

TABLE B-continued

Summary quench process parameters.

| Parameter | Value | Observation |
|---|---|---|
| Q:E ratio | 5:1 | Minimum Q:E ratio while retaining high drug encapsulation |
| Quench hold/processing temp | ≤5° C. (with current 5:1 Q:E ratio, 25:1 Tween-80:drug ratio) | Temperature which prevents significant drug leaching during quench hold time and initial concentration step |

The temperature must remain cold enough with a dilute enough suspension (low enough concentration of solvents) to remain below the $T_g$ of the particles. If the Q:E ratio is not high enough, then the higher concentration of solvent plasticizes the particles and allows for drug leakage. Conversely, colder temperatures allow for high drug encapsulation at low Q:E ratios (to ~3:1), making it possible to run the process more efficiently.

The nanoparticles are then isolated through a tangential flow filtration process to concentrate the nanoparticle suspension and buffer exchange the solvents, free drug, and drug solubilizer from the quench solution into water. A regenerated cellulose membrane is used with a molecular weight cutoffs (MWCO) of 300.

A constant volume diafiltration (DF) is performed to remove the quench solvents, free drug and Tween-80. To perform a constant-volume DF, buffer is added to the retentate vessel at the same rate the filtrate is removed. The process parameters for the TFF operations are summarized in Table C. Crossflow rate refers to the rate of the solution flow through the feed channels and across the membrane. This flow provides the force to sweep away molecules that can foul the membrane and restrict filtrate flow. The transmembrane pressure is the force that drives the permeable molecules through the membrane.

TABLE C

| Parameter | Optimized Value | Effect |
|---|---|---|
| Membrane Material | Regenerated cellulose - Coarse Screen Membrane | No difference in performance between RC and PES, but solvent compatibility is superior for RC. |
| Molecular Weight Cut off | 300 kDa | No difference in NP characteristics (i.e. residual tween)Increase in flux rates is seen with 500 kDa membrane but 500 kDa is not available in RC |
| Crossflow Rate | 11 L/min/m$^2$ | Higher crossflow rate led to higher flux |
| Transmembrane Pressure | 20 psid | Open channel membranes have maximum flux rates between 10 and 30 psid. Coarse channel membranes have maximum flux rates with min TMP (~20 psid). |
| Concentration of Nanoparticle Suspension for Diafiltration | 30 mg/ml | Diafiltration is most efficient at [NP] ~50 mg/ml with open channel TFF membranes based on flux rates and throughput. With coarse channel membranes the flux rate is optimized at ~30 mg/ml in the starting buffer. |
| Number of Diavolumes | ≥15 (based on flux increase) | About 15 diavolumes are needed to effectively remove tween-80. End point of diafiltration is determined by in-process control (flux increase plateau). |
| Membrane Area | ~1 m$^2$/kg | Membranes sized based on anticipated flux rates and volumes required. |

The filtered nanoparticle slurry is then thermal cycled to an elevated temperature during workup. A small portion (typically 5-10%) of the encapsulated drug is released from the nanoparticles very quickly after its first exposure to 25° C. Because of this phenomenon, batches that are held cold during the entire workup are susceptible to free drug or drug crystals forming during delivery or any portion of unfrozen storage. By exposing the nanoparticle slurry to elevated temperature during workup, this 'loosely encapsulated' drug can be removed and improve the product stability at the expense of a small drop in drug loading. 5 diavolumes is used as the amount for cold processing prior to the 25° C. treatment.

After the filtration process the nanoparticle suspension is passed through a sterilizing grade filter (0.2 µm absolute). Pre-filters are used to protect the sterilizing grade filter in order to use a reasonable filtration area/time for the process. Values are as summarized in Table D.

TABLE D

| Parameter | O Value | Effect |
| --- | --- | --- |
| Nanoparticle Suspension Concentration | 50 mg/ml | Yield losses are higher at higher [NP], but the ability to filter at 50 mg/ml obviates the need to aseptically concentrate after filtration |
| Filtration flow rate | ~1.3 L/min/m² | Filterability decreases as flow rate increases |

The filtration train is Ertel Alsop Micromedia XL depth filter M953P membrane (0.2 µm Nominal); Pall SUPRAcap with Seitz EKSP depth filter media (0.1-0.3 µm Nominal); Pall Life Sciences Supor EKV 0.65/0.2 µm sterilizing grade PES filter.

0.2 m² of filtration surface area per kg of nanoparticles for depth filters and 1.3 m² of filtration surface area per kg of nanoparticles for the sterilizing grade filters can be used.

Example 3

Cryoprotectant

Freezing a suspension of nanoemulsion nanoparticles in deionized water alone results in particle aggregation. This is believed to be due to crystallization and entanglement of PEG chains on the nanoparticle surfaces. Sugar-based excipients (sucrose, trehalose, or mannitol) can act to cryoprotect these nanoparticles under freeze/thaw conditions, with a concentrations as low as 1 wt % for dilute (~10 mg/ml) nanoparticle suspensions. One formulation includes 10 wt % sucrose, which contains excess sucrose to what is required and is the same osmolality as physiological saline.

Table E shows that 16/5 PLA-PEG co-polymer is less susceptible to freeze-thaw aggregation.

TABLE E

| Description | Original Median PSD/PD | Post-F/T Median PS (nm) | Post-F/T Poly-dispersity | Post-F/T Baseline Index |
| --- | --- | --- | --- | --- |
| 1:1 45/5 and PLA (baseline) | 143.4, 0.124 | 358.9 | 0.358 | 0.0/23.16% |
| 16/5 PLA-PEG and PLA (1:1) | 186.7, 0.080 | 189.5 | 0.126 | 9.7/91.57% |
| 2:1:1 16/5:PLA:cetyl | 174.1, 0.084 | 232.7 | 0.146 | 0.0/61.19% |
| 2:1:1 45/5:PLA:cetyl | 111.0, 0.182 | 0 | 0 | 0.0/1.55% |
| 16/5 PLA-PEG alone | 218.8, 0.098 | 226.9 | 0.03 | 7.3/60.56% |
| 16/5 PLA-PEG and PLA (3:1) | 222.2, 0.126 | 230.7 | 0.065 | 4.1/35.36% |
| 45/5 PLGA-PEG and PLA (3:1) | 162.7, 0.099 | 178.6 | 0.091 | 7.7/95.41% |
| 2:1:1 45/5 PLA-PEG:PLA:cetyl | 115.9, 0.154 | 734.6 | 0.392 | 0.0/13.27% |

Example 4

In vitro Release

An in vitro release method is used to determine the initial burst phase release from nanoparticles at both ambient and 37° C. conditions. In order to maintain sink conditions and prevent nanoparticles from entering the release samples, a dialysis system was designed. After obtaining an ultracentrifuge capable of pelleting 100 nm particles, the dialysis membranes were eliminated and centrifugation was used to separate released drug from encapsulated drug.

The dialysis system is as follows: 3 mL slurry of vinorelbine nanoparticles (approx 250 µg/mL vinorelbine PLGA/PLA nanoparticles, corresponding to 2.5 mg/mL solid concentration) in DI-water is placed into the inner tube of a 300 kDa MWCO dialyzer by pipetting. The nanoparticle is suspended in this media. The dialyzer is placed into a glass bottles containing 130 ml release media (2.5% hydroxyl beta cyclodextrin in PBS), which is continually stirred at 150 rpm using a shaker to prevent the formation of an unstirred water layer at the membrane/outer solution interface. At pre-determined time points, aliquot of samples (1 mL) were withdrawn from the outer solution (dialysate) and analyzed for vinorelbine concentration by HPLC.

The centrifugal system is run using similar conditions at lower suspension volumes without dialysis bags. Samples are centrifuged at 60,000 g for 30 minutes and the supernatant is assayed for vinorelbine content to measured released vinorelbine.

Example 5

Particle Size Analysis

Particle size is analyzed by two techniques—dynamic light scattering (DLS) and laser diffraction. DLS is performed using a Brookhaven ZetaPals instrument at 25° C. in dilute aqueous suspension using a 660 nm laser scattered at 90° and analyzed using the Cumulants and NNLS methods (TP008). Laser diffraction is performed with a Horiba LS950 instrument in dilute aqueous suspension using both a HeNe laser at 633 nm and an LED at 405 nm, scattered at 90° and analyzed using the Mie optical model (TP009). The output from the DLS is associated with the hydrodynamic radius of the particles, which includes the PEG 'corona', while the laser diffraction instrument is more closely associated with the geometric size of the PLA particle 'core'.

Example 6

Vinorelbine Nanoparticles

Nanoparticle batches were prepared using the general procedure of Example 2, with 80% (w/w) Polymer-PEG or Polymer-PEG with homopolymer PLA at 40% (w/w) each, with a batch of % total solids of 5%, 15% and 30%. Solvents used were: 21% benzyl alcohol and 79% ethyl acetate (w/w). For each 2 gram batch size, 400 mg of drug was used and 1.6 g of 16-5 Polymer-PEG or 0.8 g of 16-5 Polymer-PEG+0.8 g of 10 kDa PLA (homopolymer) was used. The diblock polymer 16-5 PLA-PEG or PLGA-PEG (50:50 L:G) was used, and if used, the homopolymer: PLA with a Mn=6.5 kDa, Mw=10 kDa, and Mw/Mn=1.55.

The organic phase (drug and polymer) is prepared in 2 g batches: To 20 mL scintillation vial add drug and polymer(s). The mass of solvents needed at % solids concentration is shown below:
  i. 5% solids: 7.98 g benzyl alcohol+30.02 g ethyl acetate
  ii. 15% solids: 2.38 g benzyl alcohol+8.95 g ethyl acetate
  iii. 30% solids: 0.98 g benzyl alcohol+3.69 g ethyl acetate An aqueous solution is prepared with 0.5% sodium cholate, 2% benzyl alcohol, and 4% ethyl acetate in water. Add to the bottle 7.5 g sodium cholate, 1402.5 g of DI water, 30 g of benzyl alcohol and 60 g of ethyl acetate, and mix on stir plate until dissolved.

For the formation of emulsion, a ratio of aqueous phase to oil phase is 5:1. The organic phase is poured into the aqueous solution and homogenized using IKA for 10 seconds at room temperature to form course emulsion. The solution is fed through the homogenizer (110S) at 9 Kpsi (45 psi on gauge) for 2 discreet passes to form nanoemulsion.

The emulsion is poured into quench (D.I. water) at <5° C. while stirring on stir plate. Ratio of quench to emulsion is 8:1. 35% (w/w) Tween 80 is added in water to quench at ratio of 25:1 Tween 80 to drug. The nanoparticles are concentrated through TFF and the quench is concentrated on TFF with 500 kDa Pall cassette (2 membrane) to ~100 mL. Diafiltering is used using ~20 diavolumes (2 liters) of cold DI water, and the volume is brought down to minimal volume then collect final slurry, ~100 mL. The solids concentration of unfiltered final slurry is determined by the using tared 20 mL scintillation vial and adding 4 mL final slurry and dry under vacuum on lyo/oven and the weight of nanoparticles in the 4 mL of slurry dried down is determined. Concentrated sucrose (0.666 g/g) is added to final slurry sample to attain 10% sucrose.

Solids concentration of 0.45 um filtered final slurry was determined by filtering about 5mL of final slurry sample before addition of sucrose through 0.45 µm syringe filter; to tared 20 mL scintillation vial add 4 mL of filtered sample and dry under vacuum on lyo/oven.

The remaining sample of unfiltered final slurry was frozen with sucrose.

Vinorelbine Formulations:

| % Solids | In-vitro release conducted | Polymer Type: | % Vinorelbine Load (HPLC) | Particle Size (nm) |
|---|---|---|---|---|
| 5% |  | 16-5 PLA-PEG | 4.27 | 143.3 |
|  |  | 16-5 PLA-PEG + PLA | 3.39 | 105.7 |
| 15% |  | 16-5 PLA-PEG | 6.2 | 100.3 |
|  |  | 16-5 PLA-PEG + PLA | 15.95 | 141.3 |
| 30% |  | 16-5 PLA-PEG (n = 3) | 10.41 | 90.8 |
|  |  |  | 10.31 | 84.4 |
|  | * |  | 12.01 | 95 |
|  | * | 16-5 PLA-PEG + PLA | 15.03 | 125.5 |
|  | * | 16-5 PLGA-PEG + PLA | 14.66 | 120.3 |

*= in-vitro release done on samples

Figure 7:
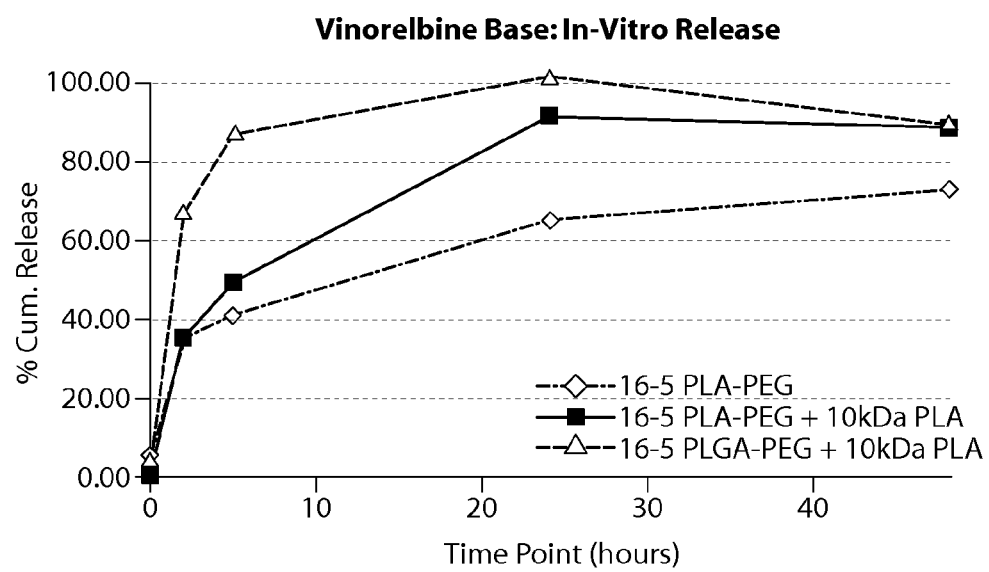
FIG. 7 depicts in vitro release properties of an exemplary disclosed nanoparticle that includes vinorelbine.

In-vitro release was conducted on three formulations at 30% totals solids: 16-5 PLA-PEG; 16-5 PLA-PEG+PLA; and 16-5 PLGA-PEG+PLA, and the in-vitro release data was collected at 37° C. in an air chamber using 10% urea in PBS solution as the release media. The table below and FIG. 7 depicts the results:

| Time Point (hours) | 16-5 PLA-PEG | 16-5 PLA-PEG + 10 kDa PLA | 16-5 PLGA-PEG + 10 kDa PLA |
|---|---|---|---|
| 0 | 5.62 | 0.84 | 4.79 |
| 2 | 35.29 | 35.35 | 67.63 |
| 5 | 41.28 | 49.58 | 87.05 |
| 24 | 65.20 | 91.81 | 101.62 |
| 48 | 73.02 | 88.63 | 89.57 |
| 144 | 81.08 | 84.98 | 91.46 |

Example 7

Vincristine Nanoparticles

Nanoparticle formulations that include vincristine were prepared using the general procedure of Example 2.

Vincristine Formulations

| Ref. No. | Components | Composition by Wt. (%) |
|---|---|---|
| 50-103-3-5 | mPEG(5k)-lPLA(16K)/Vincristine | 96/4 |
| 50-117-1-5 | mPEG(5k)-lPLA(16K)/Vincristine | 95/5 |
| 50-117-2-5 | mPEG(5k)-lPLA(16K)/Vincristine | 96/4 |
| 50-103-4 | mPEG(5k)-lPLA(16K)/lPLA(16K)/Vincristine | 46/46/8 |
| 50-103-2 | mPEG(5k)-lPLA(16K)/lPLA(16K)/Vincristine | 47/47/6 |

Analytical Characterization of Vincristine Formulations:

| Ref. No. | Size (nm) | Drug Load (%) | Encapsulation Efficiency (%) |
|---|---|---|---|
| 50-103-3-5 | 103 | 4.4 | 21.8 |
| 50-117-1-5 | 110 | 4.6 | 22.8 |
| 50-117-2-5 | 115 | 4.2 | 20.8 |
| 50-103-4 | 146 | 8.3 | 41.6 |
| 50-103-2 | 98 | 6.0 | 30.0 |

Figure 8:
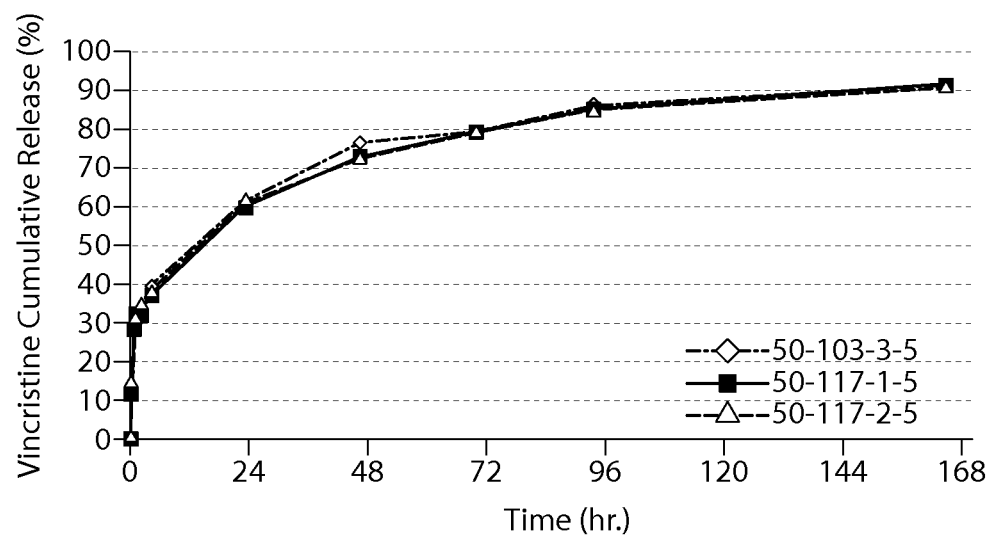
FIG. 8 depicts in vitro release properties of an exemplary disclosed nanoparticle that includes vincristine.

In vitro release was conducted on the vincristine formulations, and the in vitro release data was collected at 37° C. in an air chamber using 10% urea in PBS solution as the release media. FIG. 8 depicts in-vitro release for several of these nanoparticles.

Example 8

Pharmacokinetics

The pharmacokinetics (PK) of nanoparticles having vincristine as prepared in Example 7 were determined in Sprague-Dawley (SD) rats. Rats (male Sprague Dawley, approximately 300 g with jugular cannulae) were given a single intravenous dose of 0.5 mg/kg free drug or passively targeted nanoparticles encapsulating drug (10 wt % drug, 90 wt polymer (PLA-PEG, Mn PLA=16 Da; Mn PEG=5 Da, PTNP) with 5 mg/kg drug and PTNP at time=0. At various times after dosing, blood samples were collected from the jugular cannulae into tubes containing lithium heparin, and plasma was prepared. Plasma levels were determined by extraction of the drugs from plasma followed by LCMS analysis.

Figure 9:
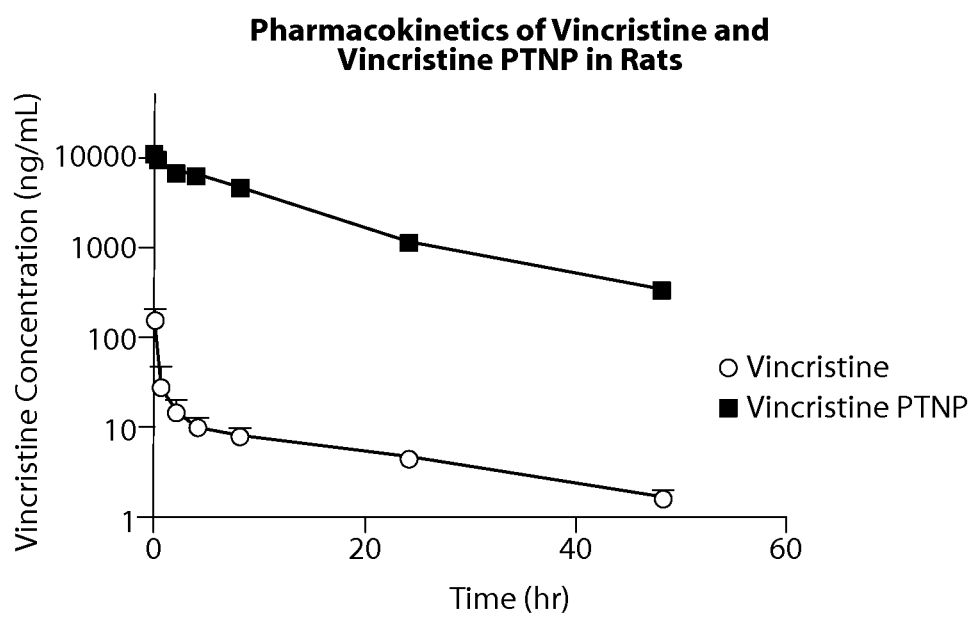
FIG. 9 depicts the pharmacokinetics of vincristine and vincristine PTNP in rats.

FIG. 9 depicts the PK profiles of vincristine and vincristine PTNP.

Equivalents

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

The entire contents of all patents, published patent applications, websites, and other references cited herein are hereby expressly incorporated herein in their entireties by reference.

The invention claimed is:

1. A therapeutic nanoparticle comprising:
about 2 to about 20 weight percent of a vinca alkaloid; and
about 70 to about 98 weight percent biocompatible polymer, wherein the biocompatible polymer is a diblock poly(lactic) acid-poly(ethylene)glycol copolymer, wherein said diblock poly(lactic) acid-poly(ethylene)glycol copolymer comprises poly(lactic acid) having a number average molecular weight of about 15 to about 20 kDa and poly(ethylene)glycol having a number average molecular weight of about 4 to about 6 kDa, and wherein a diameter of the therapeutic nanoparticle is about 70 to about 140 nm.

2. The therapeutic nanoparticle of claim 1, wherein said vinca alkaloid is vinorelbine or vincristine or a pharmaceutically acceptable salt thereof.

3. The therapeutic nanoparticle of claim 1, wherein the diameter is about 80 to about 130 nm.

4. The therapeutic nanoparticle of claim 1, comprising about 9 to about 16 weight percent of a vinca alkaloid compound.

5. The therapeutic nanoparticle of claim 1, comprising about 3 to about 9 weight percent of a vinca alkaloid compound.

6. The therapeutic nanoparticle of claim 1, wherein the particle releases less than about 2% of the vinca alkaloid, over about 1 minute to about 30 minutes, when placed in a phosphate buffer solution at room temperature.

7. The therapeutic nanoparticle of claim 1, wherein the particle releases less than about 7% of the vinca alkaloid, over about 1 minute to about 30 minutes, when placed in a phosphate buffer solution at room temperature.

8. The therapeutic nanoparticle of claim 1, wherein the particle releases less than about 10% of the vinca alkaloid, over about 1 minute to about 30 minutes, when placed in a phosphate buffer solution at 37° C.

9. The therapeutic nanoparticle of claim 1, wherein said diblock poly(lactic) acid-poly(ethylene)glycol copolymer comprises poly(lactic acid) having a number average molecular weight of about 16 kDa and poly(ethylene)glycol having a number average molecular weight of about 5 kDa.

10. The therapeutic nanoparticle of claim 1, wherein said therapeutic nanoparticle comprises about 10 weight percent to about 20 weight percent vinorelbine or a pharmaceutically acceptable salt thereof.

11. The therapeutic nanoparticle of claim 1, wherein said therapeutic nanoparticle comprises about 3 weight percent to about 10 weight percent vincristine or a pharmaceutically acceptable salt thereof.

12. The therapeutic nanoparticle of claim 1, further comprising about 0.2 to about 10 weight percent of a diblock poly(lactic)-co-poly (glycolic) acid-poly(ethylene)glycol copolymer covalently bound to a targeting ligand.

13. A pharmaceutically acceptable composition comprising a plurality of therapeutic nanoparticles of claim 1; and
a pharmaceutically acceptable excipient.

14. The pharmaceutically acceptable composition of claim 13, wherein the pharmaceutically acceptable excipient is a sugar.

15. The pharmaceutically acceptable composition of claim 14, wherein the pharmaceutically acceptable excipient is sucrose.

16. A therapeutic nanoparticle comprising:
about 2 to about 20 weight percent of a vinca alkaloid; and
a diblock polymer of poly(lactic) acid-poly(ethylene)glycol copolymer, wherein said poly(lactic) acid-poly(ethylene)glycol copolymer comprises poly(lactic acid) having a number average molecular weight of about 15 to 20 kDa and poly(ethylene)glycol having a number average molecular weight of about 4 to about 6 kDa,
wherein the diameter of the nanoparticle is about 70 to about 140 nm.

17. The therapeutic nanoparticle of claim 16, further comprising a poly(lactic) acid homopolymer having a weight average molecular weight of about 10 kDa.

18. The therapeutic nanoparticle of claim 16, wherein the therapeutic nanoparticle comprises about 40 to about 45 weight percent diblock polymer and about 40 to about 45 weight percent homopolymer.

19. The therapeutic nanoparticle of claim 16, wherein the particle releases less than about 4% of the therapeutic agent, over about 1 minute to about 30 minutes, when placed in a phosphate buffer solution at room temperature.

20. The therapeutic nanoparticle of claim 16, wherein the particle releases less than about 2% of the therapeutic agent, over about 1 minute to about 30 minutes, when placed in a phosphate buffer solution at room temperature.

21. The therapeutic nanoparticle of claim 16, further comprising cetyl alcohol.

22. A controlled release therapeutic nanoparticle comprising:
about 10 to about 20 weight percent of a vinca alkaloid;
a diblock polymer of poly(lactic) acid-poly(ethylene)glycol copolymer, wherein said poly(lactic) acid-poly(ethylene)glycol copolymer comprises poly(lactic acid) having a number average molecular weight of about 15 to 20 kDa and poly(ethylene)glycol having a number average molecular weight of about 4 to about 6 kDa, wherein the diameter of the nanoparticle is about 70 to about 140 nm, and wherein said vinca alkaloid is released at a controlled release rate.

23. The controlled release therapeutic nanoparticle of claim 22, wherein said vinca alkaloid is released over a period of at least 1 day or more when administered to a patient.

* * * * *